(12) United States Patent
Lahousse et al.

(10) Patent No.: US 11,478,414 B2
(45) Date of Patent: *Oct. 25, 2022

(54) AQUEOUS LIQUID COSMETIC COMPOSITION COMPRISING ALKYLCELLULOSE, NON-VOLATILE OILS AND AT LEAST ONE SURFACTANT

(71) Applicant: L'OREAL, Paris (FR)

(72) Inventors: Florence Lahousse, Thiais (FR); Emilie Nguyen-Henin, Vitry sur Seine (FR)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/735,035

(22) Filed: Jan. 6, 2020

(65) Prior Publication Data

US 2020/0214963 A1    Jul. 9, 2020

Related U.S. Application Data

(63) Continuation of application No. 14/370,335, filed as application No. PCT/EP2012/076311 on Dec. 20, 2012.

(60) Provisional application No. 61/603,982, filed on Feb. 28, 2012.

(30) Foreign Application Priority Data

Jan. 2, 2012 (FR) ...................................... 1250017

(51) Int. Cl.
| | |
|---|---|
| A61K 8/73 | (2006.01) |
| A61Q 1/04 | (2006.01) |
| A61K 8/34 | (2006.01) |
| A61K 8/31 | (2006.01) |
| A61K 8/891 | (2006.01) |
| A61Q 1/06 | (2006.01) |
| A61Q 19/00 | (2006.01) |

(52) U.S. Cl.
CPC ............... *A61K 8/731* (2013.01); *A61K 8/31* (2013.01); *A61K 8/342* (2013.01); *A61K 8/891* (2013.01); *A61Q 1/04* (2013.01); *A61Q 1/06* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 2,230,063 A | 1/1941 | Klimist | |
| 4,683,134 A | 7/1987 | Palinczar | |
| 4,699,779 A | 10/1987 | Palinczar | |
| 4,797,273 A | 1/1989 | Linn et al. | |
| 5,641,493 A | 6/1997 | Date et al. | |
| 5,665,368 A | 9/1997 | Lentini et al. | |
| 5,747,013 A | 5/1998 | Mougin et al. | |
| 5,849,834 A | 12/1998 | Matsuzaki et al. | |
| 5,908,631 A | 6/1999 | Arnaud et al. | |
| 6,001,374 A | 12/1999 | Nichols | |
| 6,039,960 A | 3/2000 | Chung et al. | |
| 6,387,405 B1 | 5/2002 | Shah et al. | |
| 10,292,918 B2* | 5/2019 | Lahousse | A61K 8/8111 |
| 10,292,928 B2* | 5/2019 | Lahousse | A61K 8/87 |
| 2002/0015683 A1 | 2/2002 | Nichols et al. | |
| 2002/0022009 A1 | 2/2002 | De La Poterie et al. | |
| 2003/0077962 A1 | 4/2003 | Krzysik et al. | |
| 2004/0081633 A1 | 4/2004 | Mercier et al. | |
| 2004/0197284 A1 | 10/2004 | Auguste | |
| 2005/0008667 A1 | 1/2005 | Liechty et al. | |
| 2005/0244442 A1 | 11/2005 | Sabino et al. | |
| 2005/0276763 A1 | 12/2005 | Pfeifer et al. | |
| 2006/0013789 A1 | 1/2006 | Blin et al. | |
| 2006/0019848 A1 | 1/2006 | Lou et al. | |

(Continued)

FOREIGN PATENT DOCUMENTS

| | | |
|---|---|---|
| DE | 31 12943 A1 | 10/1982 |
| DE | 698 32 545 T2 | 9/2006 |

(Continued)

OTHER PUBLICATIONS

Susan C. Smolinske "Handbook of Food, Drug, and Cosmetic Excipients" CRC Press LLC, 1992, p. 231 (with cover pages).

(Continued)

*Primary Examiner* — Lakshmi S Channavajjala

(74) *Attorney, Agent, or Firm* — Oblon, McClelland, Maier & Neustadt, L.L.P.

(57) ABSTRACT

The present invention relates to a liquid cosmetic composition comprising, in a physiologically acceptable medium:
  at least 20% of water,
  at least alkylcellulose, preferably at least 1% of alkylcellulose,
  at least one first hydrocarbon-based non-volatile oil, chosen from:
    $C_{10}$-$C_{26}$ alcohols, preferably monoalcohols;
    optionally hydroxylated monoesters, diesters or triesters of a $C_2$-$C_8$ monocarboxylic or polycarboxylic acid and of a $C_2$-$C_8$ alcohol;
    esters of a $C_2$-$C_8$ polyol and of one or more $C_2$-$C_8$ carboxylic acids,
  at least one second non-volatile oil chosen from silicone oils and/or fluoro oils;
  at least one third oil, the said third oil being chosen from hydrocarbon-based oils other than the said first oil;
  at least one surfactant, preferably non-ionic.

16 Claims, No Drawings

(56) References Cited

U.S. PATENT DOCUMENTS

| | | | |
|---|---|---|---|
| 2006/0051486 A1* | 3/2006 | Dowdell | A61Q 17/04 426/601 |
| 2006/0088483 A1 | 4/2006 | Thevenet | |
| 2011/0038820 A1 | 2/2011 | Barba et al. | |
| 2013/0046029 A1 | 2/2013 | Germaneau et al. | |
| 2013/0049513 A1 | 2/2013 | Germaneau et al. | |
| 2013/0280197 A1* | 10/2013 | Geffroy | A61K 8/345 424/64 |
| 2013/0280198 A1* | 10/2013 | Cavazutti | A61Q 19/00 424/64 |
| 2014/0377203 A1* | 12/2014 | Lahousse | A61K 8/87 424/64 |

FOREIGN PATENT DOCUMENTS

| | | |
|---|---|---|
| EP | 0 336 902 A2 | 10/1989 |
| EP | 0 795 318 A2 | 9/1997 |
| EP | 0 823 250 A2 | 2/1998 |
| EP | 0 861 657 A2 | 9/1998 |
| EP | 1 051 968 A2 | 11/2000 |
| EP | 1 192 937 A2 | 4/2002 |
| EP | 1 604 635 A2 | 12/2005 |
| EP | 1 604 644 A1 | 12/2005 |
| EP | 1 913 929 A2 | 4/2008 |
| EP | 2 116 221 A1 | 11/2009 |
| EP | 2 599 472 B1 | 11/2016 |
| FR | 2 771 628 A1 | 6/1999 |
| FR | 2 771 629 A1 | 6/1999 |
| FR | 2 918 272 A1 | 1/2009 |
| FR | 2 921 266 B1 | 6/2012 |
| FR | 2 978 037 B1 | 1/2014 |
| GB | 795841 | 5/1958 |
| JP | H10-067624 A | 3/1998 |
| JP | 2000-219617 A | 8/2000 |
| KR | 10-2010-0103708 A | 9/2010 |
| WO | WO 96/36310 A1 | 11/1996 |
| WO | WO 2005/046626 A2 | 5/2005 |
| WO | WO 2006/017203 A1 | 2/2006 |
| WO | WO 2007/026101 A1 | 3/2007 |
| WO | WO 2009/006218 A2 | 1/2009 |
| WO | WO 2009/080953 A2 | 7/2009 |
| WO | WO 2009/080958 A2 | 7/2009 |
| WO | WO 2009/105294 A2 | 8/2009 |
| WO | WO-2011/100275 A1 * | 8/2011 ............... A61K 8/37 |
| WO | WO 2012/038879 A2 | 3/2012 |
| WO | WO 2012/064714 A2 | 5/2012 |
| WO | WO 2013/088051 A2 | 6/2013 |
| WO | WO 2013/102727 A1 | 7/2013 |

OTHER PUBLICATIONS

"Glossy Full Couleur Extreme Shine Lip Gloss", Make Up For Ever, Product No. 1522027, Mar. 2011, 3 pages.
Marie Contier et al., "Characterization of the tack and gloss of cosmetic formulations", LVMH Recherche Parfums & Cosmetiques Materials Innovation Department, May 13, 2016, pp. 1-5 (with English translation).
Written Opinion dated Jul. 21, 2008 in French Patent Application No. 0854940.
"Basic Properties of PARLEAM®", NOF Corporation Oleo & Specialty Chemicals Div., Apr. 2015, 2 pages.
"Report on tests carried out by the company L'Oréal in response to the notice of opposition formed by the company Parfums Christian Dior against patent EP 2 618 803 B1", L'Oréal, Jun. 19, 2017, pp. 1-3 (with English translation).
"ETHOCEL", Ethylcellulose Polymers Technical Handbook, Dow Cellulosics, Sep. 2005, pp. 1-28.
Charles M. Hansen, "The Three Dimensional Solubility Parameter—Key to Paint Component Affinities: I. Solvents, Plasticizers, Polymers, and Resins", Journal of Paint Technology, vol. 39, No. 505, Feb. 1967, pp. 104-117.
Notice of Opposition dated Jan. 6, 2017 in European Patent Application No. 2 618 803 B1 (with English translation).
Response to Notice of Opposition dated Jun. 19, 2017 in European Patent Application No. 2 618 803 (with English translation).
"Colour Gloss Extension", MINTEL No. 10116327, Aug. 2002, 2 pages.
"Final Report of the Cosmetic Ingredient Review Expert Panel on the Safety Assessment of Polyisobutene and Hydrogenated Polyisobutene as Used in Cosmetics", International Journal of Toxicology, 27 (Suppl. 4) pp. 83-106, 2008.
Mar. 11, 2016 Office Action issued in U.S. Appl. No. 13/824,548.
Oct. 21, 2015 Notice of Opposition issued in European Patent Application No. 2 618 811.
Nov. 4, 2015 Office Action issued in U.S. Appl. No. 13/824,533.
Mar. 11, 2015 Office Action issued in U.S. Appl. No. 13/824,533.
Dec. 24, 2014 Office Action issued in Japanese Application No. 2013-528824.
Flirt-Tinis Protective Lip Balm, XP-002731953, Sep. 2008, pp. 1-3.
Tendertones SPF12 (Purring), XP-002731954, Aug. 2007, pp. 1-2.
Lip Moisture Cream SPF 30, XP-002731955, Apr. 2006, pp. 1-3.
Nov. 13, 2014 Search Report and Written Opinion issued in French Application No. 1452985.
Nov. 14, 2013 Office Action issued in Korean Application No. 10-2013-7018815.
Nov. 28, 2013 Office Action issued in Korean Application No. 10-2013-7021162.
"Octyldodecyl Stearoyl Stearate", SAAPedia, http://www.saapedia.org/en/saa/?type=detail&id=2994, pp. 1-2, accessed Feb. 26, 2015.
"Hydrocarbon", Wikipedia, http://en.wikipedia.org/wiki/Hydrocarbon, pp. 1-5, accessed Feb. 26, 2015.
"Triethanolamine", Wikipedia, http://en wikipedia.ord/wiki/Triethanolamine, pp. 1-6, accessed Feb. 26, 2015.
Mar. 10, 2015 Office Action issued in Chinese Application No. 201180055831.3.
International Search Report issued in International Patent Application No. PCT/EP2011/066208 dated Mar. 29, 2012.
International Preliminary Report on Patentability issued in International Patent Application No. PCT/EP2011/066208 dated Mar. 26, 2013.
Oct. 31, 2012 French Search Report and Written Opinion issued in French Patent Application 1250017 (with translation).
Oct. 31, 2012 Written Opinion issued in French Patent Application 1250017.
"Smooth Cover Gel", Database GNPD [Online] Mintel, Sep. 2009, XP-002658176.
"Mousse Foundation Natural Bronzing Effect", Database GNPD [Online] Mintel, Nov. 2010, XP-002658177.
"Ceramide Moisture Network Night Cream [Ingredients]", Database GNPD [Online] Mintel, Sep. 2004, XP-002658178.
"Beauty Body Gel", Database GNPD [Online] Mintel, Sep. 2010, XP-002658179.
"Butter Shine Lipstick", Database GNPD [Online] Mintel, Oct. 2008, XP-002658180.
"Lip Polish", Database GNPD [Online] Mintel, Jun. 2010, XP-002658181.
"Liquid Foundation", Database GNPD [Online] Mintel, Sep. 2010, XP-002658182.
May 6, 2011 French Search Report and Written Opinion issued in French Patent Application No. FR 1057526 (with translation).
May 6, 2011 French Search Report and Written Opinion issued in French Patent Application No. FR 1057528 (with translation).
Sep. 5, 2011 French Search Report and Written Opinion issued in French Patent Application No. FR 1060600 (with translation).
Sep. 5, 2011 French Search Report and Written Opinion issued in French Patent Application No. FR 1060650 (with translation).
Sep. 5, 2011 French Search Report and Written Opinion issued in French Patent Application No. FR 1060652 (with translation.
Apr. 3, 2012 Written Opinion of the International Searching Authority issued in International Application No. PCT/IB2011/054087.
Mar. 26, 2013 International Preliminary Report on Patentability issued in International Application No. PCT/IB2011/054087.
Apr. 3, 2012 International Search Report issued in International Application No. PCT/IB2011/054087.

(56) References Cited

OTHER PUBLICATIONS

Melzer, Eva et al., "Ethylcellulose: a new type of emulsion stabilizer", European Journal of Pharmaceutics and Biopharmaceuticals, 56:23-27, 2003.
"Making Emulsions for Cosmetics", makingcosmetics.com, Oct. 12, 2004.
Google search results for "cosmetic and emulsion", Nov. 30, 2014.
Dec. 18, 2014 Office Action issued in U.S. Appl. No. 13/824,548.
Mar. 10, 2014 Office Action issued in U.S. Appl. No. 13/824,548.
Feb. 13, 2014 Office Action issued in U.S. Appl. No. 13/824,548.
U.S. Appl. No. 13/824,548, filed Jul. 10, 2013.
U.S. Appl. No. 13/824,533, filed Mar. 20, 2013.
"Why balsam and vanishing cream in the cosmetics are classified as "water-in-oil" type and a "oil-in-water" type?", ISBN 7-5023-2244-2, 1995, 5 pages (with English Translation).
Arbonne product "Lip Polish" Technical Document, 2015, 2 pages.

\* cited by examiner

AQUEOUS LIQUID COSMETIC COMPOSITION COMPRISING ALKYLCELLULOSE, NON-VOLATILE OILS AND AT LEAST ONE SURFACTANT

This application claims the benefit of priority from U.S. application Ser. No. 14/370,335, filed Jul. 2, 2014, which is a 371 of PCT/EP2012/076311, filed Dec. 20, 2012, which claims benefit of U.S. Application No. 61/603,982 filed Feb. 28, 2012, and of prior French Application No. 1250017, filed Jan. 2, 2012 the entire contents of which is hereby incorporated by reference.

The present invention is directed towards proposing liquid cosmetic compositions comprising alkylcellulose, which are intended in particular for making up and/or caring for the lips or the skin, especially the lips, which are capable of producing a deposit, especially a makeup deposit, which shows good cosmetic properties, especially in terms of comfort, absence of tack and gloss.

In general, cosmetic compositions need to afford an aesthetic effect when applied to the skin and/or the lips, and to maintain this aesthetic effect over time.

Specifically, the production of an aesthetic effect, after applying a cosmetic composition, results from an assembly of properties intrinsic to the composition which are expressed in terms of makeup performance, cosmetic properties such as comfort on application (ease of application, glidance on application) and while wearing the composition (freshness and/or no sensation of pulling), satisfactory homogeneity, lightness and gloss of the deposit produced with the composition.

In particular, the production of a liquid composition which is homogeneous and stable over time at 24° C. and at 45° C., and whose deposit on the skin or the lips is uniform, fresh and light and sufficiently glossy without developing tack, is an ongoing preoccupation of formulators working in the field of lipsticks and other skincare and/or lipcare products.

Ethylcellulose is already known in cosmetic and/or therapeutic compositions, as a film-forming agent, for facilitating the formation of a film on the skin and/or the lips, and for improving the water resistance of this film.

Unfortunately, ethylcellulose, and alkylcelluloses in general (with an alkyl group comprising from 1 to 6 carbon atoms), is of limited solubility in the majority of the solvents commonly used in cosmetic and/or dermatological formulations. In general, monoalcohols containing from 2 to 8 carbon atoms, such as ethanol, butanol, methanol or isopropanol, are preferred for dissolving sufficient amounts of ethylcellulose in cosmetic or pharmaceutical compositions. Evaporation of the $C_2$-$C_8$ monoalcohols leads, after application of the corresponding cosmetic composition to the skin or the lips, firstly to concentration of the deposit and secondly to the formation of a coat on the surface of the skin or the lips that has a very good wear property. For example, document WO 96/36310 proposes cosmetic compositions especially comprising ethylcellulose dissolved in ethyl alcohol (SDA 38B-190 or SDA 40B-190 solvents).

However, these volatile monoalcohols have the drawback of being potentially irritant to the skin and/or the lips, and consequently may prove to be detrimental in the case of repeated use on the skin.

In order to overcome this problem, it has been proposed in document U.S. Pat. No. 5,908,631 to use, as an alternative to $C_2$-$C_8$ monoalcohols, a certain number of solvents for ethylcellulose, such as lanolin oil, certain triglycerides, certain propylene glycol or neopentyl glycol esters, isostearyl lactate, and mixtures thereof.

Unfortunately, replacing these $C_2$-$C_8$ monoalcohols, which are volatile compounds, with these non-volatile solvents may on the other hand prove to be detrimental in terms of comfort and of a fresh sensation and lightness of the resulting deposit.

Consequently, there is still a need for cosmetic compositions, which are free of $C_2$-$C_8$ monoalcohols, comprising a sufficient amount of alkylcellulose, and which are capable of forming on the skin and/or the lips a deposit that has gloss and comfort properties and that is sparingly tacky or non-tacky.

There is more particularly a need for compositions for making up and/or caring for the skin and/or the lips, which are homogeneous and stable over time (especially for 72 hours at 24° C. and for 72 hours at 45° C.), in particular which do not undergo phase separation, which are easy to apply and which allow the production of a uniform, light, fresh, non-migrating deposit which, in particular, is sparingly tacky or non-tacky and satisfactorily glossy.

One aim of the invention is to propose a composition whose texture is homogeneous and stable at 24° C. and at 45° C.

The object of the present invention is, precisely, to satisfy these needs.

As emerges from the examples presented below, the inventors have discovered that the abovementioned expectations can be satisfied by formulating the alkylcellulose in the form of a dispersion in water with a mixture of specific oils other than $C_2$-$C_8$ monoalcohols.

Thus, according to a first of its aspects, a subject of the present invention is a liquid cosmetic composition comprising, in a physiologically acceptable medium:
  at least 20% of water, preferably at least 30% of water;
  at least alkylcellulose, the alkyl residue of which comprises between 1 and 6 carbon atoms, preferably between 2 and 6 carbon atoms and preferably between 2 and 3 carbon atoms, preferably ethylcellulose;
  at least one first oil, the said first oil being a hydrocarbon-based non-volatile oil, chosen from:
    $C_{10}$-$C_{26}$ alcohols, preferably monoalcohols;
    optionally hydroxylated monoesters, diesters or triesters of a $C_2$-$C_8$ monocarboxylic or polycarboxylic acid and of a $C_2$-$C_8$ alcohol;
    esters of a $C_2$-$C_8$ polyol and of one or more $C_2$-$C_8$ carboxylic acids,
  at least one second oil, the said second oil being a non-volatile oil chosen from silicone oils and/or fluoro oils;
  at least one third oil, the said third oil being chosen from hydrocarbon-based oils other than the said first oil;
  at least one, preferably nonionic surfactant.

Advantageously, a cosmetic composition according to the invention is homogeneous, stable (no exudation or phase separation) over time (especially after 72 hours or even 1 month at 24° C. and at 45° C.), easy to apply to the skin and/or the lips, and produces a uniform, fine, light and fresh deposit that is non-migrating and without a sensation of dryness or pulling, non-tacky or sparingly tacky, and satisfactorily glossy.

The composition according to the invention is in liquid form at 20° C.

The term "liquid" is intended to mean a composition capable of flowing under its own weight, at 20° C. and at atmospheric pressure (760 mmHg), as opposed to compositions said to be as "solid".

Preferably, the composition is a composition for making up and/or caring for the skin and/or the lips. According to a preferred embodiment, the composition is a lip product. Preferably, the cosmetic composition according to the invention is a liquid lipstick, such as a gloss for example or a "stain" for the lips.

The term "stain" is intended to mean a very fluid composition whose viscosity is less than that of a conventional gloss. A lip stain may be applied with a lip brush for example, and makes it possible to obtain a finer deposit than that obtained with a conventional gloss composition for the lips. In general, the thickness of a film obtained with a composition of "stain" type is preferably between 5 μm and 30 μm, preferably between 5 and 20 μm.

The composition according to the invention also concerns a process for making up and/or caring for the skin and/or the lips, preferably the lips.

A composition according to the invention also proves to be particularly suitable for the use of water-soluble dyes.

As emerges from the examples below, the combination of the oils under consideration according to the invention proves to be particularly advantageous for formulating alkylcelluloses, preferably such as ethylcellulose, in the said composition.

A composition according to the invention advantageously allows the use of an effective amount of alkylcellulose. For the purposes of the present invention, the term "effective amount" means an amount that is sufficient to obtain the expected effect, as described previously.

In particular, a composition according to the invention comprises at least 1% and particularly preferably at least 2% by weight (solids) of alkylcellulose (preferentially ethylcellulose) relative to the total weight of the composition.

Particularly preferably, the composition according to the invention comprises from 2% to 60% by weight of alkylcellulose (preferably ethylcellulose), more preferably from 2.5% to 30% by weight and more preferably still from 3% to 20% by weight, relative to the total weight of the composition.

The term "physiologically acceptable medium" is intended to denote a medium that is particularly suitable for the application of a composition according to the invention to the skin and/or the lips.

Preferably, the composition according to the invention has a viscosity at 20° C. of less than 1.5 Pa·s.

Preferably, the composition according to the invention comprises a viscosity of between 0.05 and 1.5 Pa·s, preferably between 0.08 and 1 Pa·s. According to this embodiment, the viscosity of a gloss and of a stain is included.

According to a particularly preferred embodiment, the composition according to the invention has a viscosity of between 0.1 and 0.7 Pa·s.

Protocol for Measuring the Viscosity:

According to this embodiment, when the composition according to the invention is in the form of a paste at 20° C. (the term "paste" or "butter" means a composition that is therefore not solid, and whose viscosity can be measured), its viscosity may be measured according to the following protocol:

The viscosity measurement is carried out at 20° C., using a Rheomat RM180 viscometer equipped with a No. 2 spindle for the very fluid formula (whose viscosity is less than 0.7 Pa·s) or with a No. 3 spindle for the slightly thicker formulae whose viscosity is greater than 0.7 Pa·s, and in particular between 0.7 and 1.5 Pa·s, the measurement being carried out after rotating the spindle for 10 minutes (at the end of which time stabilization of the viscosity and of the rotational speed of the spindle are observed), at a shear rate of 200 s−1.

The composition according to the invention has at 20° C. a viscosity of between 0.05 and 1.5 Pa·s and preferably between 0.08 and 1 Pa·s.

Particularly preferably, the viscosity at 20° C. of a composition according to the invention is between 0.1 and 0.7 Pa·s.

A composition according to the invention is preferably in the form of an emulsion of oil in an aqueous phase, conventionally known as an "oil-in water emulsion".

According to one particular embodiment, a composition of the invention comprises less than 5% by weight of silicone surfactant(s), in particular less than 4% by weight, especially less than 3% by weight, more particularly less than 2% by weight and in particular less than 1% by weight, or even is totally free of silicone surfactant.

According to another of its aspects, a subject of the present patent application is a cosmetic process for making up and/or caring for the lips and/or the skin, in particular the lips, comprising at least one step that consists in applying to the lips and/or the skin at least one composition as defined previously.

Ethylcellulose

A composition according to the invention comprises at least alkylcellulose, the alkyl residue of which comprises between 1 and 6 carbon atoms, preferably between 2 and 6 carbon atoms and preferably between 2 and 3 carbon atoms, preferably ethylcellulose.

According to one particularly preferred embodiment, the alkylcellulose (preferentially of $C_2$ to $C_6$, preferentially ethylcellulose) is present in a composition according to the invention in a content (solids) ranging from 1% to 60% by weight.

Particularly preferably, the composition according to the invention comprises from 2% to 30% by weight of alkylcellulose (preferentially of C2 to C6), and more preferably still from 2.5% to 20% by weight, relative to the total weight of the said composition.

The alkylcellulose is a cellulose alkyl ether comprising a chain formed from β-anhydroglucose units linked together via acetal bonds. Each anhydroglucose unit contains three replaceable hydroxyl groups, all or some of these hydroxyl groups being able to react according to the following reaction:

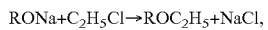

$$RONa + C_2H_5Cl \rightarrow ROC_2H_5 + NaCl,$$

in which R represents a cellulose radical.

Advantageously, the alkylcellulose is chosen from methylcellulose, ethylcellulose and propylcellulose.

According to one particularly preferred embodiment, the alkylcellulose is ethylcellulose.

It is a cellulose ethyl ether.

Total substitution of the three hydroxyl groups would lead for each anhydroglucose unit to a degree of substitution of 3, in other words to a content of alkoxy groups of 54.88%.

The ethylcellulose polymers used in a cosmetic composition according to the invention are preferentially polymers with a degree of substitution with ethoxy groups ranging from 2.5 to 2.6 per anhydroglucose unit, in other words comprising a content of ethoxy groups ranging from 44% to 50%.

According to a preferred mode, the alkylcellulose (preferably ethylcellulose) is used in a composition of the invention in the form of particles dispersed in an aqueous phase, like a dispersion of latex or pseudolatex type. The techniques for preparing these latex dispersions are well known to those skilled in the art.

The product sold by the company FMC Biopolymer under the name Aquacoat ECD-30, which consists of a dispersion of ethylcellulose at a rate of about 26.2% by weight in water and stabilized with sodium lauryl sulfate and cetyl alcohol, is most particularly suitable for use as an aqueous dispersion of ethylcellulose.

According to one particular embodiment, the aqueous dispersion of ethylcellulose, in particular the product Aquacoat ECD, may be used in a proportion of from 3% to 90% by weight, in particular from 5% to 60% by weight and preferably from 5% to 50% by weight of ethylcellulose dispersion relative to the total weight of the composition.

As mentioned previously, the alkylcellulose is used according to the present invention in combination with a mixture of oils as described more particularly hereinbelow.

Physiologically Acceptable Medium

Besides the compounds indicated previously, a composition according to the invention comprises a physiologically acceptable medium.

The term "physiologically acceptable medium" is intended to denote a medium that is particularly suitable for applying a composition of the invention to the skin and/or the lips, for instance water, the oils or organic solvents commonly used in cosmetic compositions.

The physiologically acceptable medium (acceptable tolerance, toxicology and feel) is generally adapted to the nature of the support onto which the composition is to be applied, and also to the form in which the composition is to be conditioned.

Fatty Phase

The composition according to the invention comprises at least one fatty phase and especially a liquid fatty phase, at least a first specific hydrocarbon-based non-volatile oil and at least a second non-volatile oil chosen from silicone oils and/or fluoro oils. The term "oil" means a water-immiscible non-aqueous compound that is liquid at room temperature (25° C.) and at atmospheric pressure (760 mmHg).

Specific First Hydrocarbon-Based Non-Volatile Oil

The composition according to the invention comprises one or more first hydrocarbon-based non-volatile oil(s), chosen from:
$C_{10}$-$C_{26}$ alcohols, preferably monoalcohols;
optionally hydroxylated monoesters, diesters or triesters of a $C_2$-$C_8$ monocarboxylic or polycarboxylic acid and of a $C_2$-$C_8$ alcohol;
esters of a $C_2$-$C_8$ polyol and of one or more $C_2$-$C_8$ carboxylic acids.

The term "non-volatile" refers to an oil whose vapour pressure at room temperature and atmospheric pressure is non-zero and is less than 0.02 mmHg (2.66 Pa) and better still less than $10^{-3}$ mmHg (0.13 Pa).

Preferably, the said "first oil" is chosen from:
$C_{10}$-$C_{26}$ monoalcohols;
optionally hydroxylated monoesters of a $C_2$-$C_8$ carboxylic acid and of a $C_2$-$C_8$ alcohol;
optionally hydroxylated diesters of a $C_2$-$C_8$ dicarboxylic acid and of a $C_2$-$C_8$ alcohol;
optionally hydroxylated triesters of a $C_2$-$C_8$ tricarboxylic acid and of a $C_2$-$C_8$ alcohol;
esters of a $C_2$-$C_8$ polyol and of one or more $C_2$-$C_8$ carboxylic acids.

The term "hydrocarbon-based oil" means an oil formed essentially from, constituted by, carbon and hydrogen atoms, and possibly oxygen atoms, and free of heteroatoms such as N, Si, F and P. The hydrocarbon-based oil is thus different from a silicone oil or a fluoro oil.

In the present case, the said first oils comprise at least one oxygen atom.

In particular, the said first non-volatile hydrocarbon-based oil comprises at least one alcohol function (it is then an "alcohol oil") and/or at least one ester function (it is then an "ester oil").

The ester oils that may be used in the compositions according to the invention may especially be hydroxylated.

According to one particular embodiment, a composition according to the invention comprises one or more first non-volatile hydrocarbon-based oil(s) in a content ranging from 2% to 75%, preferably ranging from 5% to 50%, in particular from 5% to 40% by weight relative to its total weight.

According to one particularly preferred embodiment, the non-volatile hydrocarbon-based oil and the alkylcellulose (in particular ethylcellulose) are used in the composition according to the invention in a "non-volatile hydrocarbon-based first oil(s)/alkylcellulose" weight ratio of between 0.5 and 20 and preferably between 1 and 15. Particularly preferably, the "non-volatile hydrocarbon-based first oil(s)/alkylcellulose" weight ratio is between 2 and 10.

More particularly, the first non-volatile hydrocarbon-based first oil used in a composition according to the invention may especially have plasticizing properties, i.e. it can impart suppleness and comfort to the deposit formed with the composition according to the invention.

According to a particularly preferred embodiment, the said first oil is a $C_{10}$-$C_{26}$ alcohol, preferably a monoalcohol, which is preferably branched when it comprises at least 16 carbon atoms.

Preferably, the $C_{10}$-$C_{26}$ alcohols are saturated or unsaturated, and branched or unbranched, and comprise from 10 to 26 carbon atoms. Preferably, the $C_{10}$-$C_{26}$ alcohols are fatty alcohols, which are preferably branched when they comprise at least 16 carbon atoms.

As examples of fatty alcohols that may be used according to the invention, mention may be made of linear or branched fatty alcohols, of synthetic origin or alternatively of natural origin, for instance alcohols derived from plant material (coconut, palm kernel, palm, etc.) or animal material (tallow, etc.). Needless to say, other long-chain alcohols may also be used, for instance ether alcohols or Guerbet alcohols. Finally, use may also be made of certain more or less long fractions of alcohols of natural origin, for instance coconut ($C_{12}$ to $C_{16}$) or tallow ($C_{16}$ to $C_{18}$) or compounds of diol or cholesterol type.

Use is preferably made of a fatty alcohol comprising from 10 to 24 carbon atoms and more preferentially from 12 to 22 carbon atoms.

As particular examples of preferred fatty alcohols that may be used in the context of the present invention, mention may be made especially of lauryl alcohol, myristyl alcohol, isostearyl alcohol, palmityl alcohol, oleyl alcohol, behenyl alcohol, erucyl alcohol, arachidyl alcohol, 2-hexyldecyl alcohol, isocetyl alcohol and octyldodecanol, and mixtures thereof.

Preferably, the said first oil is chosen from octyldodecanol and isostearyl alcohol, and mixtures thereof.

Preferably, the said "first oil" is octyldodecanol.

According to a second embodiment, the said first oil is an ester oil chosen from:
optionally hydroxylated monoesters of a $C_2$-$C_8$ carboxylic acid and of a $C_2$-$C_8$ alcohol;

optionally hydroxylated diesters of a $C_2$-$C_8$ dicarboxylic acid and of a $C_2$-$C_8$ alcohol; such as diisopropyl adipate, 2-diethylhexyl adipate, dibutyl adipate or diisostearyl adipate, optionally hydroxylated triesters of a $C_2$-$C_8$ tricarboxylic acid and of a $C_2$-$C_8$ alcohol, such as citric acid esters, such as trioctyl citrate, triethyl citrate, acetyl tributyl citrate, tributyl citrate or acetyl tributyl citrate, esters of a $C_2$-$C_8$ polyol and of one or more $C_2$-$C_8$ carboxylic acids, such as glycol diesters of monoacids, such as neopentyl glycol diheptanoate, or glycol triesters of monoacids, such as triacetin.

Second Non-Volatile Silicone Oil and/or Fluoro Oil

According to one of its aspects, a composition according to the invention comprises at least a second non-volatile oil chosen from silicone oils and/or fluoro oils.

The term "non-volatile" refers to an oil whose vapour pressure at room temperature and atmospheric pressure is non-zero and is less than 0.02 mmHg (2.66 Pa) and better still less than $10^{-3}$ mmHg (0.13 Pa).

Preferably, the non-volatile oil(s) chosen from silicone oils and/or fluoro oils are present in a total content ranging from 5% to 75% by weight, preferably from 8% to 40% by weight or alternatively from 10% to 30% by weight relative to the total weight of the said composition.

According to one particular embodiment, a composition according to the invention comprises one or more non-volatile silicone oils (preferably phenyl silicone oils) and/or non-volatile fluoro oils, in a proportion of at least 5% by weight relative to the total weight of the composition, especially from 5% to 75% by weight and particularly preferably from 8% to 45% by weight.

According to one particularly preferred embodiment, the composition comprises a total content of non-volatile oils (i.e. all the non-volatile oils of the composition, irrespective of their nature) of between 10% and 60% by weight and preferably between 20% and 50% by weight relative to the total weight of the composition.

According to a particularly preferred embodiment, the non-volatile oils (i.e. all the non-volatile oils of the composition, irrespective of their nature) and the alkylcellulose are used in the composition according to the invention in a non-volatile oil(s)/alkylcellulose weight ratio of between 1 and 20 and preferably between 4 and 15.

Non-Volatile Silicone Oil

According to a first particularly preferred embodiment, the non-volatile oil is a silicone oil.

The term "silicone oil" means an oil comprising at least one silicon atom. The non-volatile silicone oil that may be used in the invention may be chosen especially from silicone oils especially with a viscosity at 25° C. of greater than or equal to 9 centistokes (cSt) ($9 \times 10^{-6}$ m$^2$/s) and less than 800 000 cSt, preferably between 50 and 600 000 cSt and preferably between 100 and 500 000 cSt. The viscosity of this silicone oil may be measured according to standard ASTM D-445.

According to a first embodiment, the non-volatile silicone oil is a non-phenyl silicone oil.

The non-volatile non-phenyl silicone oil may be chosen from:

non-volatile polydimethylsiloxanes (PDMS),

PDMSs comprising alkyl or alkoxy groups, which are pendent and/or at the end of the silicone chain, these groups each containing from 2 to 24 carbon atoms, PDMSs comprising aliphatic and/or aromatic groups, or functional groups such as hydroxyl, thiol and/or amine groups, polyalkylmethylsiloxanes optionally substituted with a fluoro group, such as polymethyltrifluoropropyldimethylsiloxanes, polyalkylmethylsiloxanes substituted with functional groups such as hydroxyl, thiol and/or amine groups, polysiloxanes modified with fatty acids, fatty alcohols or polyoxyalkylenes, and mixtures thereof.

According to one embodiment, a composition according to the invention contains at least one non-phenyl silicone oil, in particular such as a linear (i.e. non-cyclic) oil.

Representative examples of these non-volatile non-phenyl linear silicone oils that may be mentioned include polydimethylsiloxanes; alkyl dimethicones; vinyl methyl methicones; and also silicones modified with optionally fluorinated aliphatic groups, or with functional groups such as hydroxyl, thiol and/or amine groups.

The non-phenyl silicone oil may be chosen especially from the silicones of formula (I):

$$X-\underset{R_2}{\overset{R_1}{\underset{|}{\overset{|}{Si}}}}-O-\left[\underset{R_4}{\overset{R_3}{\underset{|}{\overset{|}{Si}}}}-O\right]_n-\left[\underset{R_6}{\overset{R_5}{\underset{|}{\overset{|}{Si}}}}-O\right]_p-\underset{R_2}{\overset{R_1}{\underset{|}{\overset{|}{Si}}}}-X \qquad (I)$$

in which:

$R_1$, $R_2$, $R_5$ and $R_6$ are, together or separately, an alkyl radical containing 1 to 6 carbon atoms, $R_3$ and $R_4$ are, together or separately, an alkyl radical containing from 1 to 6 carbon atoms, a vinyl radical, an amine radical or a hydroxyl radical, X is an alkyl radical containing from 1 to 6 carbon atoms, a hydroxyl radical or an amine radical, n and p are integers chosen so as to have a fluid compound, in particular whose viscosity at 25° C. is between 9 centistokes (cSt) ($9 \times 10^{-6}$ m$^2$/s) and 800 000 cSt.

As non-volatile silicone oils that may be used according to the invention, mention may be made of the compounds of formula (I) for which:

the substituents $R_1$ to $R_6$ and X represent a methyl group, and p and n are such that the viscosity is 500 000 cSt, such as the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning, the substituents $R_1$ to $R_6$ and X represent a methyl group, and p and n are such that the viscosity is 60 000 cSt, such as the product sold under the name Dow Corning 200 Fluid 60000 CS by the company Dow Corning, and the product sold under the name Wacker Belsil DM 60 000 by the company Wacker, the substituents $R_1$ to $R_6$ and X represent a methyl group, and p and n are such that the viscosity is 350 cSt, such as the product sold under the name Dow Corning 200 Fluid 350 CS by the company Dow Corning, the substituents $R_1$ to $R_6$ represent a methyl group, the group X represents a hydroxyl group, and n and p are such that the viscosity is 700 cSt, such as the product sold under the name Baysilone Fluid T0.7 by the company Momentive.

According to a second embodiment, a composition according to the invention contains at least one non-volatile phenyl silicone oil as second non-volatile oil.

Representative examples of these non-volatile phenyl silicone oils that may be mentioned include:

the phenyl silicone oils corresponding to the following formula:

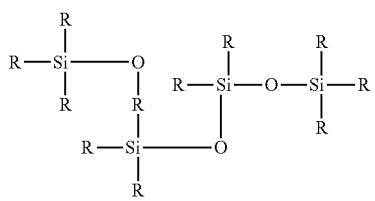
(I)

in which the groups R represent, independently of each other, a methyl or a phenyl, with the proviso that at least one group R represents a phenyl. Preferably, in this formula, the phenyl silicone oil comprises at least three phenyl groups, for example at least four, at least five or at least six.

the phenyl silicone oils corresponding to the following formula:

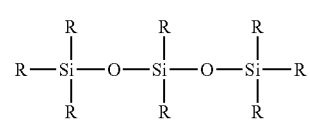
(II)

in which the groups R represent, independently of each other, a methyl or a phenyl, with the proviso that at least one group R represents a phenyl.

Preferably, in this formula, the said organopolysiloxane comprises at least three phenyl groups, for example at least four or at least five. Mixtures of the phenyl organopolysiloxanes described previously may be used. Examples that may be mentioned include mixtures of triphenyl, tetraphenyl or pentaphenyl organopolysiloxanes.

the phenyl silicone oils corresponding to the following formula:

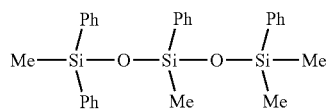
(III)

in which Me represents methyl, Ph represents phenyl. Such a phenyl silicone is especially manufactured by Dow Corning under the reference PH-1555 HRI or Dow Corning 555 Cosmetic Fluid (chemical name: 1,3,5-trimethyl-1,1,3,5,5-pentaphenyl trisiloxane; INCI name: trimethyl pentaphenyl trisiloxane). The reference Dow Corning 554 Cosmetic Fluid may also be used.

the phenyl silicone oils corresponding to the following formula:

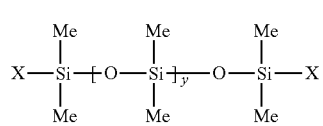
(IV)

in which Me represents methyl, y is between 1 and 1000 and X represents —$CH_2$—$CH(CH_3)(Ph)$.

the phenyl silicone oils corresponding to formula (V) below:

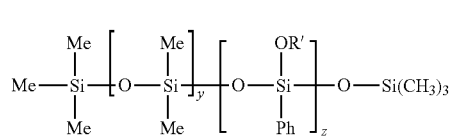
(V)

in which Me is methyl and Ph is phenyl, OR' represents a group —$OSiMe_3$ and y is 0 or ranges between 1 and 1000, and z ranges between 1 and 1000, such that compound (V) is a non-volatile oil.

According to a first embodiment, y ranges between 1 and 1000. Use may be made, for example, of trimethyl siloxyphenyl dimethicone, sold especially under the reference Belsil PDM 1000 sold by the company Wacker.

According to a second embodiment, y is equal to 0. Use may be made, for example, of phenyl trimethylsiloxy trisiloxane, sold especially under the reference Dow Corning 556 Cosmetic Grade Fluid, the phenyl silicone oils corresponding to formula (VI) below, and mixtures thereof:

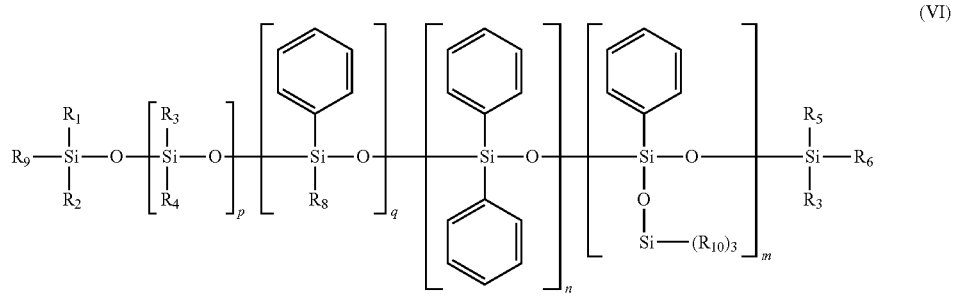
(VI)

in which:
R$_1$ to R$_{10}$, independently of each other, are saturated or unsaturated, linear, cyclic or branched C$_1$-C$_{30}$ hydrocarbon-based radicals,
m, n, p and q are, independently of each other, integers between 0 and 900, with the proviso that the sum m+n+q is other than 0.

Preferably, the sum m+n+q is between 1 and 100. Preferably, the sum m+n+p+q is between 1 and 900 and better still between 1 and 800. Preferably, q is equal to 0.

the phenyl silicone oils corresponding to formula (VII) below, and mixtures thereof:

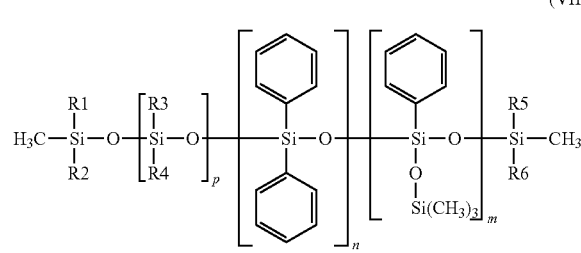

(VII)

in which:
R$_1$ to R$_6$, independently of each other, are saturated or unsaturated, linear, cyclic or branched C$_1$-C$_{30}$ hydrocarbon-based radicals,
m, n and p are, independently of each other, integers between 0 and 100, with the proviso that the sum n+m is between 1 and 100.

Preferably, R$_1$ to R$_6$, independently of each other, represent a saturated, linear or branched C$_1$-C$_{30}$ and especially C$_1$-C$_{12}$ hydrocarbon-based radical and in particular a methyl, ethyl, propyl or butyl radical.

R$_1$ to R$_6$ may especially be identical, and in addition may be a methyl radical.

Preferably, m=1 or 2 or 3, and/or n=0 and/or p=0 or 1 may apply, in formula (VII).

the phenyl silicone oils corresponding to formula (VIII), and mixtures thereof:

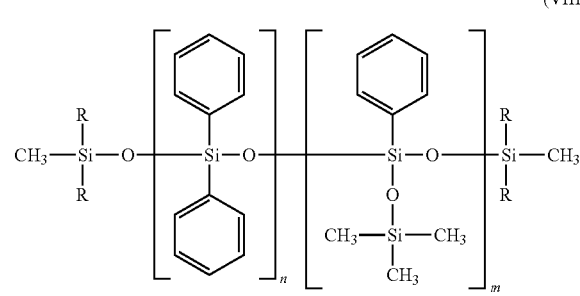

(VIII)

in which:
R is a C$_1$-C$_{30}$ alkyl radical, an aryl radical or an aralkyl radical,
n is an integer ranging from 0 to 100, and
m is an integer ranging from 0 to 100, with the proviso that the sum n+m ranges from 1 to 100.

In particular, the radicals R of formula (VIII) and R$_1$ to R$_{10}$ defined previously may each represent a linear or branched, saturated or unsaturated alkyl radical, especially of C$_2$-C$_{20}$, in particular C$_3$-C$_{16}$ and more particularly C$_4$-C$_{10}$, or a monocyclic or polycyclic C$_6$-C$_{14}$ and especially C$_{10}$-C$_{13}$ aryl radical, or an aralkyl radical whose aryl and alkyl residues are as defined previously.

Preferably, R of formula (VIII) and R$_1$ to R$_{10}$ may each represent a methyl, ethyl, propyl, isopropyl, decyl, dodecyl or octadecyl radical, or alternatively a phenyl, tolyl, benzyl or phenethyl radical.

According to one embodiment, a phenyl silicone oil of formula (VIII) with a viscosity at 25° C. of between 5 and 1500 mm$^2$/s (i.e. 5 to 1500 cSt), and preferably with a viscosity of between 5 and 1000 mm$^2$/s (i.e. 5 to 1000 cSt) may be used.

Phenyl silicone oils that may especially be used include the phenyl trimethicones of formula (VIII), such as DC556 from Dow Corning (22.5 cSt), the oil Silbione 70663V30 from Rhone-Poulenc (28 cSt) or diphenyl dimethicones such as Belsil oils, especially Belsil PDM1000 (1000 cSt), Belsil PDM 200 (200 cSt) and Belsil PDM 20 (20 cSt) from Wacker. The values in parentheses represent the viscosities at 25° C.

the phenyl silicone oils corresponding to the following formula, and mixtures thereof:

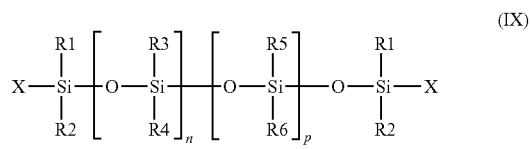

(IX)

in which:
R$_1$, R$_2$, R$_5$ and R$_6$ are, together or separately, an alkyl radical containing 1 to 6 carbon atoms,
R$_3$ and R$_4$ are, together or separately, an alkyl radical containing from 1 to 6 carbon atoms or an aryl radical,
X is an alkyl radical containing from 1 to 6 carbon atoms, a hydroxyl radical or a vinyl radical,
n and p being chosen so as to give the oil a weight-average molecular mass of less than 200 000 g/mol, preferably less than 150 000 g/mol and more preferably less than 100 000 g/mol.

the phenyl silicones are more particularly chosen from phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and mixtures thereof.

More particularly, the phenyl silicones are chosen from phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, and mixtures thereof.

Preferably, the weight-average molecular weight of the non-volatile phenyl silicone oil according to the invention ranges from 500 to 10 000 g/mol.

By way of example of preferred non-volatile silicone oils, mention may be made of the silicone oils such as:
phenyl silicones (also known as phenyl silicone oil) such as trimethylsiloxyphenyl dimethicone (for instance Belsil PDM 1000 from the company Wacker (MW=9000 g/mol) (cf. formula (V) above), phenyl trimethicones (such as the phenyl trimethicone sold under the trade name DC556 by Dow Corning), phenyl dimethicones, phenyltrimethylsiloxydiphenylsiloxanes, diphenyl dimethicones, diphenylmethyldiphenyltrisiloxanes, 2-phenylethyl trimethylsiloxysilicates, trimethylpentaphenyl trisiloxane (such as the product sold under the name Dow Corning PH-1555 HRI Cosmetic fluid by Dow Corning) (cf formula (III) above), non-volatile polydimethylsiloxanes (PDMS), polydimethylsiloxanes comprising alkyl or alkoxy groups, which are pendent and/or at the end of the silicone chain, these groups each containing from 2 to 24 carbon atoms, and mixtures thereof.

Preferably, the second non-volatile oil is a phenyl silicone oil.

Preferably, a phenyl silicone oil is used. According to one preferred embodiment, the phenyl silicone oil is chosen from trimethylsiloxyphenyl dimethicones.

According to one preferred embodiment, the non-volatile silicone oil(s) are present in a total content ranging from 5% to 75% by weight, in particular from 10% to 40% by weight and preferably from 15% to 30% by weight relative to the total weight of the said composition.

Non-Volatile Fluoro Oil

According to a second embodiment, the second non-volatile oil is a fluoro oil.

The term "fluoro oil" means an oil containing at least one fluorine atom.

The fluoro oils that may be used according to the invention may be chosen from fluorosilicone oils, fluoro polyethers and fluorosilicones as described in document EP-A-847 752, and perfluoro compounds.

According to the invention, the term "perfluoro compounds" means compounds in which all the hydrogen atoms have been replaced with fluorine atoms.

According to one particularly preferred embodiment, the fluoro oil according to the invention is chosen from perfluoro oils.

As examples of perfluoro oils that may be used in the invention, mention may be made of perfluorodecalins and perfluoroperhydrophenanthrenes.

According to one particularly preferred embodiment, the fluoro oil is chosen from perfluoroperhydrophenanthrenes, and especially the Fiflow® products sold by the company Creations Couleurs. In particular, use may be made of the fluoro oil for which the INCI name is Perfluoroperhydrophenanthrene, sold under the reference Fiflow 220 by the company F2 Chemicals.

Third Hydrocarbon-Based Oil Other than the Said First Oil

The composition according to the invention comprises a third oil, the said third oil being a hydrocarbon-based oil, which is different from the said first oil.

According to a first preferred embodiment, the third hydrocarbon-based oil is a non-volatile oil.

According to a first embodiment, the non-volatile hydrocarbon-based oil is chosen from apolar hydrocarbon-based oils.

For the purposes of the present invention, the term "apolar oil" means an oil whose solubility parameter at 25° C., $\delta_a$, is equal to 0 $(J/cm^3)^{1/2}$.

The definition and calculation of the solubility parameters in the Hansen three-dimensional solubility space are described in the paper by C. M. Hansen: "The three-dimensional solubility parameters", J. Paint Technol., 39, 105 (1967).

According to this Hansen space:

$\delta_D$ characterizes the London dispersion forces derived from the formation of dipoles induced during molecular impacts;

$\delta_p$ characterizes the Debye interaction forces between permanent dipoles and also the Keesom interaction forces between induced dipoles and permanent dipoles;

$\delta_h$ characterizes the specific interaction forces (such as hydrogen bonding, acid/base, donor/acceptor, etc.); and $\delta_a$ is determined by the equation: $\delta_a=(\delta_p^2+\delta_h^2)^{1/2}$.

The parameters $\delta_p$, $\delta_h$, $\delta_D$ and $\delta_a$ are expressed in $(J/cm^3)^{1/2}$.

Preferably, the non-volatile apolar hydrocarbon-based oil is free of oxygen atoms.

Preferably, the non-volatile apolar hydrocarbon-based oil may be chosen from linear or branched hydrocarbons of mineral or synthetic origin, such as:

liquid paraffin or derivatives thereof, liquid petroleum jelly, naphthalene oil, polybutylenes such as Indopol H-100 (molar mass or MW=965 g/mol), Indopol H-300 (MW=1340 g/mol) and Indopol H-1500 (MW=2160 g/mol) sold or manufactured by the company Amoco, hydrogenated polyisobutylenes such as Parleam® sold by the company Nippon Oil Fats, Panalane H-300 E sold or manufactured by the company Amoco (MW=1340 g/mol), Viseal 20000 sold or manufactured by the company Synteal (MW=6000 g/mol) and Rewopal PIB 1000 sold or manufactured by the company Witco (MW=1000 g/mol), decene/butene copolymers, polybutene/polyisobutene copolymers, especially Indopol L-14, polydecenes and hydrogenated polydecenes such as: Puresyn 10 (MW=723 g/mol) and Puresyn 150 (MW=9200 g/mol) sold or manufactured by the company Mobil Chemicals, and mixtures thereof.

According to a second embodiment, the non-volatile hydrocarbon-based oil is chosen from polar hydrocarbon-based oils other than the said "first oil".

In particular, the polar non-volatile oil other than the said first oil may be an ester oil, in particular containing between 18 and 70 carbon atoms.

Examples that may be mentioned include monoesters, diesters or triesters.

The ester oils may be hydroxylated. Preferably, they are not hydroxylated.

The non-volatile ester oil is preferably chosen from:

monoesters comprising between 18 and 40 carbon atoms in total, in particular the monoesters of formula $R_1COOR_2$ in which $R_1$ represents a linear or branched fatty acid residue comprising from 4 to 40 carbon atoms and $R_2$ represents a hydrocarbon-based chain, which is especially branched, containing from 4 to 40 carbon atoms, on condition that $R_1+R_2 \geq 18$, for instance Purcellin oil (cetostearyl octanoate), isononyl isononanoate, $C_{12}$ to $C_{15}$ alkyl benzoates, 2-ethylhexyl palmitate, octyldodecyl neopentanoate, 2-octyldodecyl stearate, 2-octyldodecyl erucate, isostearyl isostearate, 2-octyldodecyl benzoate, alcohol or polyalcohol octanoates, decanoates or ricinoleates, isopropyl myristate, isopropyl palmitate, butyl stearate, hexyl laurate, 2-ethylhexyl palmitate, 2-hexyldecyl laurate, 2-octyldecyl palmitate, 2-octyldodecyl myristate or 2-diethylhexyl succinate. Preferably, they are esters of formula $R_1COOR_2$ in which $R_1$ represents a linear or branched fatty acid residue containing from 4 to 40 carbon atoms and $R_2$ represents a hydrocarbon-based chain that is especially branched, containing from 4 to 40 carbon atoms provided that $R_1+R_2 \geq 18$. Preferably, the ester comprises between 18 and 40 carbon atoms in total. Preferred monoesters that may be mentioned include isononyl isononanoate, oleyl erucate and/or 2-octyldodecyl neopentanoate;

diesters, especially comprising between 18 and 60 carbon atoms in total and in particular between 18 and 50 carbon atoms in total. It is especially possible to use diesters of dicarboxylic acids and of monoalcohols, preferably such as diisostearyl malate, or glycol diesters of monocarboxylic acids, such as neopentyl glycol diheptanoate or poly-2-glyceryl diisostearate (especially such as the compound sold under the trade reference Dermol DGDIS by the company Alzo);

triesters, especially comprising between 35 and 70 carbon atoms in total, in particular such as triesters of a tricarboxylic acid, such as triisostearyl citrate, or tridecyl trimellitate, or glycol triesters of monocarboxylic acids such as poly-2-glyceryl triisostearate;

tetraesters, especially with a total carbon number ranging from 35 to 70, such as pentaerythritol or polyglycerol tetraesters of a monocarboxylic acid, for instance pentaerythrityl tetrapelargonate, pentaerythrityl tetraisostearate, pentaerythrityl tetraisononanoate, glyceryl tris(2-decyl)tetradecanoate, poly-2-glyceryl tetraisostearate or pentaerythrityl tetrakis(2-decyl)tetradecanoate;

polyesters obtained by condensation of an unsaturated fatty acid dimer and/or trimer and of diol, such as those described in patent application FR 0 853 634, in particular such as dilinoleic acid and 1,4-butanediol. Mention may especially be made in this respect of the polymer sold by Biosynthis under the name Viscoplast 14436H (INCI name: dilinoleic acid/butanediol copolymer), or copolymers of polyols and of diacid dimers, and esters thereof, such as Hailuscent ISDA;

esters and polyesters of diol dimer and of monocarboxylic or dicarboxylic acid, such as esters of diol dimer and of fatty acid and esters of diol dimer and of dicarboxylic acid dimer, in particular which may be obtained from a dicarboxylic acid dimer derived in particular from the dimerization of an unsaturated fatty acid especially of $C_8$ to $C_{34}$, especially of $C_{12}$ to $C_{22}$, in particular of $C_{16}$ to $C_{20}$ and more particularly of $C_{18}$, such as esters of dilinoleic diacids and of dilinoleic diol dimers, for instance those sold by the company Nippon Fine Chemical under the trade names Lusplan DD-DA5® and DD-DA7®;

vinylpyrrolidone/1-hexadecene copolymers, for instance the product sold under the name Antaron V-216 (also known as Ganex V216) by the company ISP (MW=7300 g/mol), hydrocarbon-based plant oils such as fatty acid triglycerides (which are liquid at room temperature), especially of fatty acids containing from 7 to 40 carbon atoms, such as heptanoic or octanoic acid triglycerides or jojoba oil; mention may be made in particular of saturated triglycerides such as caprylic/capric triglycerides and mixtures thereof, for instance the product sold under the reference Myritol 318 from Cognis, glyceryl triheptanoate, glyceryl trioctanoate, and $C_{18-36}$ acid triglycerides such as those sold under the reference Dub TGI 24 sold by Stéarineries Dubois, and unsaturated triglycerides such as castor oil, olive oil, ximenia oil and pracaxi oil;

and mixtures thereof.

According to one preferred embodiment, the third oil is an apolar and preferably non-volatile hydrocarbon-based oil. Preferably, according to this embodiment, it is chosen from liquid paraffin, liquid petroleum jelly, naphthalene oil, polybutylenes, hydrogenated polyisobutylenes, decene/butene copolymers, polybutene/polyisobutene copolymers, polydecenes and hydrogenated polydecenes, and mixtures thereof.

According to a preferred embodiment, the composition comprises a total content of third oil(s), which are preferably non-volatile, ranging from 0.5% to 40% by weight, preferably ranging from 1% to 30% by weight and more preferably from 2% to 20% by weight relative to the total weight of the composition.

According to a second embodiment, the third hydrocarbon-based oil is a volatile oil.

For the purposes of the invention, the term "volatile oil" means an oil that is capable of evaporating on contact with keratin materials in less than one hour, at room temperature and atmospheric pressure (760 mmHg). The volatile organic solvent(s) and volatile oils of the invention are volatile organic solvents and cosmetic oils that are liquid at room temperature, with a non-zero vapour pressure at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg), and more particularly ranging from 1.3 Pa to 1300 Pa (0.01 to 10 mmHg).

Preferably the hydrocarbon-based volatile oil is an apolar oil.

The apolar volatile hydrocarbon-based oil may have a flash point ranging from 40° C. to 102° C., preferably ranging from 40° C. to 55° C. and preferentially ranging from 40° C. to 50° C.

The hydrocarbon-based volatile oil may especially be chosen from hydrocarbon-based volatile oils containing from 8 to 16 carbon atoms, and mixtures thereof, and especially:

branched $C_8$-$C_{16}$ alkanes such as $C_8$-$C_{16}$ isoalkanes (also known as isoparaffins), isododecane, isodecane and isohexadecane, and, for example, the oils sold under the trade name Isopar or Permethyl, linear alkanes, for example such as n-dodecane (C12) and n-tetradecane (C14) sold by Sasol under the references, respectively, Parafol 12-97 and Parafol 14-97, and also mixtures thereof, the undecane-tridecane mixture (Cetiol UT), mixtures of n-undecane (C11) and of n-tridecane (C13) obtained in Examples 1 and 2 of patent application WO 2008/155 059 from the company Cognis, and mixtures thereof.

According to one particular embodiment, the hydrocarbon-based volatile oil(s) may be present in a content ranging from 0.1% to 30% by weight and especially from 0.5% to 20% by weight relative to the total weight of the said composition.

Advantageously, the composition contains less than 10% by weight of monoalcohols containing from 1 to 5 carbon atoms, and preferably less than 5%. According to one particular embodiment, the composition may be free of monoalcohols containing from 1 to 5 carbon atoms.

According to a preferred embodiment, the composition is free of volatile oil.

According to one particular embodiment, the composition comprises a total content of third oil(s) ranging from 0.5% to 40% by weight, preferably ranging from 1% to 30% by weight and more preferably from 2% to 20% by weight relative to the total weight of the composition.

Preferably, the composition comprises between 2% and 30% by weight of alkylcellulose, preferably ethylcellulose, between 30% and 85% by weight of water and between 10% and 50% by weight of non-volatile oils.

Additional Oils

The composition according to the invention may comprise, besides the non-volatile hydrocarbon-based "first oil" and besides the non-volatile "second oil" chosen from silicone oils and/or fluoro oils and besides the third hydrocarbon-based oil other than the said first oil, at least one additional oil other than these oils.

In particular, the additional oil may be chosen from volatile silicone oils and/or volatile fluoro oils.

According to a first embodiment, the additional volatile oil is a silicone oil and may be chosen especially from silicone oils with a flash point ranging from 40° C. to 102° C., preferably with a flash point of greater than 55° C. and less than or equal to 95° C., and preferentially ranging from 65° C. to 95° C.

As additional volatile silicone oils that may be used in the invention, mention may be made of linear or cyclic silicones with a viscosity at room temperature of less than 8 centistokes (cSt) ($8\times10^{-6}$ m$^2$/s), and especially containing from 2 to 10 silicon atoms and in particular from 2 to 7 silicon atoms, these silicones optionally comprising alkyl or alkoxy groups containing from 1 to 10 carbon atoms. As volatile silicone oils that may be used in the invention, mention may be made especially of dimethicones with viscosities of and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

According to a second embodiment, the additional volatile oil is a fluoro oil, such as nonafluoromethoxybutane or perfluoromethylcyclopentane, and mixtures thereof.

According to a preferred embodiment, the composition is free of additional oil.

Solid Fatty Substances:

Wax(es)

The composition according to the invention may comprise at least one solid fatty substance chosen from waxes, pasty fatty substances and mixtures thereof.

For the purposes of the invention, the term "wax" means a lipophilic compound, which is solid at room temperature (25° C.), with a reversible solid/liquid change of state, which has a melting point of greater than or equal to 30° C., which may be up to 120° C.

The waxes that may be used in a composition according to the invention are chosen from solid waxes that may or may not be deformable at room temperature of animal, plant, mineral or synthetic origin, and mixtures thereof.

Hydrocarbon-based waxes, for instance beeswax, lanolin wax or Chinese insect wax; rice wax, carnauba wax, candelilla wax, ouricury wax, esparto grass wax, cork fibre wax, sugar cane wax, Japan wax and sumach wax; montan wax, microcrystalline waxes, paraffins and ozokerite; polyethylene waxes, polymethylene waxes, the waxes obtained by Fisher-Tropsch synthesis and waxy copolymers, and also esters thereof, may especially be used.

Mention may also be made of waxes obtained by catalytic hydrogenation of animal or plant oils containing linear or branched $C_8$-$C_{32}$ fatty chains.

Among these waxes that may especially be mentioned are hydrogenated jojoba oil, hydrogenated sunflower oil, hydrogenated castor oil, hydrogenated coconut oil, hydrogenated lanolin oil, bis(1,1,1-trimethylolpropane) tetrastearate sold under the name Hest 2T-4S by the company Heterene, and bis(1,1,1-trimethylolpropane) tetrabehenate sold under the name Hest 2T-4B by the company Heterene.

Waxes that may also be mentioned include silicone waxes ($C_{30-45}$ alkyl dimethicone) and fluoro waxes.

Waxes that may also be used include those obtained by hydrogenation of castor oil esterified with cetyl alcohol, sold under the names Phytowax ricin 16L64® and 22L73® by the company Sophim. Such waxes are described in patent application FR-A-2 792 190.

A wax that may be used is a $C_{20}$-$C_{40}$ alkyl (hydroxystearyloxy)stearate (the alkyl group containing from 20 to 40 carbon atoms), alone or as a mixture. Such a wax is especially sold under the names Kester Wax K 82 P®, Hydroxypolyester K 82 P® and Kester Wax K 80 P® by the company Koster Keunen.

Preferably, the said wax(es) are chosen from waxes whose melting point (Tm) is less than or equal to 66° C. and preferably less than or equal to 65° C.

Preferably, the wax with a Tm of less than or equal to 66° C. and preferably less than or equal to 65° C. is chosen from: candelilla wax (64.3° C.), polyglycerolated beeswax (63.1° C.), ceresin wax (60.1° C.), Ultrabee WD (61.3° C.), pentaerythrityl tetrastearate (63.0° C.), tetracontanyl stearate (65.1° C.), fatty acid wax (63.7° C.); beeswax (62.6° C.), Montan wax (63.4° C.), sucrose polybehenate (64.1° C.), Koster KPC-60 (61.7° C.), Koster KPC-63 (65.2° C.), the hydrogenated esters of olive oil and of stearyl alcohol (57° C.) sold under the reference Phytowax Olive 18 L 57 by the company Sophim, the hydrogenated palm oil sold under the reference GV 60 by SIO (ADM), the polymethylene wax (54° C.) sold under the reference Cirebelle 303 by Cirebelle; the polymethylene wax (40° C.) sold under the reference Cirebelle 505 by Cirebelle, the glyceryl tribehenate (60° C.) sold under the reference Syncrowax HRC-PA-(MH) by Croda, and mixtures thereof.

Preferably, the composition may comprise at least one polymethylene wax, preferably chosen from the polymethylene wax (54° C.) sold under the reference Cirebelle 303 by Cirebelle; the polymethylene wax (40° C.) sold under the reference Cirebelle 505 by Cirebelle.

According to one particularly preferred embodiment, the composition is free of wax with a Tm of greater than 66° C.

The reason for this is that during the preparation of a composition according to the invention, the introduction of a wax with a Tm of greater than 66° C., for instance polyethylene wax, microcrystalline wax or carnauba wax, may lead to the formation of lumps and balls, and thus prevent the production of a smooth, homogeneous composition.

Illustrations of such waxes are especially carnauba wax (82.3° C.), ozokerite (66.8° C.), microcrystalline wax (83.3° C.), the polyethylene wax sold, for example, under the name Asensa SC 211 by Honeywell (95.6° C.), the wax AC 540 (98.4° C.), hydroxyoctacosanyl hydroxystearate (76.8° C.), hydrogenated castor waxes (81.7° C.), the wax AC400 (86.3° C.), the polyethylene wax sold, for example, under the name Performalene 500-L Polyethylene from New Phase Technologies (77.3° C.), hydrogenated jojoba wax (69.4° C.), rice bran wax (78.6° C.), the tricontanyl/PVP copolymer (68.8° C.), octacosanyl stearate (72.5° C.), the polyethylene wax sold, for example, under the name Performalene 400 Polyethylene from New Phase Technologies (71.8° C.), the polyethylene wax sold, for example, under the name Performalene 655 Polyethylene from New Phase Technologies (92.9° C.), polyethylenated alcohol wax (95.7° C.), Koster K82P (69.6° C.), polymethylalkyl dimethylsiloxane (67.8° C.), polyethylene related alcohol wax (76.2° C.), Fischer-Tropsch wax (79.3° C.), behenyl alcohol (66.9° C.), Chinese insect wax (81.1° C.), shellac wax (73.8° C.), behenyl fumarate (74.5° C.), didotricontanyl distearate (70.7° C.), Betawax RX-13750 (72.0° C.), dipentaerythrityl hexastearate (67.7° C.), ditrimethylolpropane tetrabehenate (67.5° C.), Phytowax Ricin 16 L 64 (69.1° C.), Phytowax Ricin 22 L 73 (76.6° C.), ouricury wax (81.0° C.), and mixtures thereof.

Emulsifying Silicone Wax:

According to one particular embodiment, the composition according to the invention comprises at least one emulsifying silicone wax, preferably such as the product INCI whose name is BIS-PEG-18 methyl ether dimethyl silane, sold especially under the reference Dow Corning 2501 Cosmetic Wax by Dow Corning.

The composition according to the invention may comprise from 1% to 20% by weight and better still between 2% and 15%, by total weight, of this emulsifying silicone wax relative to the total weight of the composition.

According to a particular embodiment of the invention, the composition does not comprise additional wax other than BIS-PEG-18 methyl ether dimethyl silane.

Preferably, the wax is chosen from candelilla wax and/or polymethylene wax, and/or the wax BIS-PEG-18 methyl ether dimethyl silane; and mixtures thereof.

Preferably, the wax is a polymethylene wax.

Preferably, the total wax content is between 0% and 5% by weight and especially between 0.1% and 3% by weight, relative to the total weight of the composition.

According to a preferred embodiment of the invention, the composition according to the invention is free of wax.

Pasty Fatty Substances

The composition under consideration according to the invention may also comprise at least one pasty fatty substance.

For the purposes of the present invention, the term "pasty fatty substance" (also known as pasty fatty substance) means a lipophilic fatty compound with a reversible solid/liquid change of state, exhibiting an anisotropic crystalline organization in the solid state, and comprising, at a temperature of 23° C., a liquid fraction and a solid fraction.

In other words, the starting melting point of the pasty compound can be less than 23° C. The liquid fraction of the pasty compound, measured at 23° C., can represent from 9% to 97% by weight of the compound. This liquid fraction at 23° C. preferably represents between 15% and 85% and more preferably between 40% and 85% by weight.

Within the meaning of the invention, the melting point corresponds to the temperature of the most endothermic peak observed in thermal analysis (DSC) as described in Standard ISO 11357-3; 1999. The melting point of a pasty substance or of a wax may be measured using a differential scanning calorimeter (DSC), for example the calorimeter sold under the name MDSC 2920 by the company TA Instruments.

The measuring protocol is as follows:

A sample of 5 mg of paste or wax (depending on the case) placed in a crucible is subjected to a first temperature rise passing from −20° C. to 100° C., at the heating rate of 10° C./minute, then is cooled from 100° C. to −20° C. at a cooling rate of 10° C./minute and finally subjected to a second temperature rise passing from −20° C. to 100° C. at a heating rate of 5° C./minute. During the second temperature rise, the variation in the difference in power absorbed by the empty crucible and the crucible containing the sample of pasty substance or wax is measured as a function of the temperature. The melting point of the compound is the value of the temperature corresponding to the tip of the peak of the curve representing the variation in the difference in power absorbed as a function of the temperature.

The liquid fraction by weight of the pasty compound at 23° C. is equal to the ratio of the enthalpy of fusion consumed at 23° C. to the enthalpy of fusion of the pasty compound.

The enthalpy of fusion of the pasty compound is the enthalpy consumed by the compound in order to change from the solid state to the liquid state. The pasty compound is said to be in the solid state when all of its mass is in crystalline solid form. The pasty compound is said to be in the liquid state when all of its mass is in liquid form.

The heat of fusion of the pasty compound is equal to the area under the curve of the thermogram obtained using a differential scanning calorimeter (DSC), such as the calorimeter sold under the name MDSC 2920 by the company TA Instrument, with a temperature rise of 5° C. or 10° C. per minute, according to standard ISO 11357-3:1999. The enthalpy of fusion of the pasty compound is the amount of energy necessary to make the compound change from the solid state to the liquid state. It is expressed in J/g.

The heat of fusion consumed at 23° C. is the amount of energy absorbed by the sample to change from the solid state to the state that it has at 23° C., composed of a liquid fraction and a solid fraction.

The liquid fraction of the pasty compound measured at 32° C. preferably represents from 30% to 100% by weight of the compound, preferably from 50% to 100%, more preferably from 60% to 100% by weight of the compound. When the liquid fraction of the pasty compound measured at 32° C. is equal to 100%, the temperature of the end of the melting range of the pasty compound is less than or equal to 32° C.

The liquid fraction of the pasty compound measured at 32° C. is equal to the ratio of the enthalpy of fusion consumed at 32° C. to the enthalpy of fusion of the pasty compound. The enthalpy of fusion consumed at 32° C. is calculated in the same way as the enthalpy of fusion consumed at 23° C.

The pasty fatty compound may preferably be chosen from synthetic compounds and compounds of plant origin. A pasty fatty substance may be obtained by synthesis from starting materials of plant origin.

The pasty compound is advantageously chosen from:
  lanolin and derivatives thereof, such as lanolin alcohol, oxyethylenated lanolins, acetylated lanolin, lanolin esters such as isopropyl lanolate, and oxypropylenated lanolins;
  petrolatum, in particular the product which has this as INCI name and which is sold under the name Ultima White PET USP by Penreco;
  polyol ethers chosen from ethers of pentaerythritol and of polyalkylene glycol, ethers of fatty alcohol and of sugar, and mixtures thereof, the ethers of pentaerythritol and of polyethylene glycol comprising 5 oxyethylene units (5 OE) (CTFA name: PEG-5 Pentaerythrityl Ether), the polypropylene glycol pentaerythrityl ether comprising 5 oxypropylene (5 OP) units (CTFA name: PPG-5 Pentaerythrityl Ether) and mixtures thereof, and more especially the mixture PEG-5 Pentaerythrityl Ether, PPG-5 Pentaerythrityl Ether and soybean oil, sold under the name Lanolide by the company Vevy, which is a mixture in which the constituents are in a 46/46/8 weight ratio: 46% PEG-5 Pentaerythrityl Ether, 46% PPG-5 Pentaerythrityl Ether and 8% soybean oil;
  polymeric or non-polymeric silicone compounds;
  polymeric or non-polymeric fluoro compounds;

vinyl polymers, in particular:
olefin homopolymers and copolymers, and especially vinylpyrrolidone/eicosene copolymers, for instance the product sold under the name Antaron V-220 (also known as Ganex V220) by the company ISP,
hydrogenated diene homopolymers and copolymers,
oligomers that are linear or branched homopolymers or copolymers of alkyl (meth)acrylates preferably containing a $C_8$-$C_{30}$ alkyl group,
oligomers that are homopolymers and copolymers of vinyl esters containing $C_8$-$C_{30}$ alkyl groups,
oligomers that are homopolymers and copolymers of vinyl ethers having $C_8$-$C_{30}$ alkyl groups,
liposoluble polyethers resulting from polyetherification between one or more $C_2$-$C_{100}$ and preferably $C_2$-$C_{50}$ diols,
esters,
and/or their mixtures.

The pasty compound is preferably a polymer, in particular a hydrocarbon polymer.

Preference is given in particular, among the fat-soluble polyethers, to copolymers of ethylene oxide and/or of propylene oxide with long-chain $C_6$-$C_{30}$ alkylene oxides, more preferably such that the ratio by weight of the ethylene oxide and/or of the propylene oxide to the alkylene oxides in the copolymer is from 5:95 to 70:30. In this family, mention will be made in particular of copolymers such that the long-chain alkylene oxides are positioned in blocks having an average molecular weight from 1000 to 10 000, for example a polyoxyethylene/polydodecyl glycol block copolymer, such as the ethers of dodecanediol (22 mol) and of polyethylene glycol (45 OE) sold under the brand name Elfacos ST9 by Akzo Nobel.

Preference is given in particular, among the esters, to:
esters of an oligomeric glycerol, in particular diglycerol esters, especially condensates of adipic acid and of glycerol, for which a portion of the hydroxyl groups of the glycerols have reacted with a mixture of fatty acids, such as stearic acid, capric acid, stearic acid and isostearic acid, and 12-hydroxystearic acid, preferably such as bis-diglyceryl polyacyladipate-2, sold under the brand name Softisan 649 by Sasol,
vinyl ester homopolymers containing $C_8$-$C_{30}$ alkyl groups, such as polyvinyl laurate (sold especially under the reference Mexomer PP by the company Chimex) and arachidyl propionate sold under the brand name Waxenol 801 by Alzo,
phytosterol esters,
fatty acid triglycerides and their derivatives, such as, for example, triglycerides of fatty acids, in particular $C_{10}$-$C_{18}$ fatty acids, which are partially or completely hydrogenated, such as those sold under the reference Softisan 100 by Sasol,
pentaerythritol esters,
non-crosslinked polyesters resulting from polycondensation between a linear or branched $C_4$-$C_{50}$ dicarboxylic acid or polycarboxylic acid and a $C_2$-$C_{50}$ diol or polyol,
aliphatic esters of an ester resulting from the esterification of an aliphatic hydroxycarboxylic acid ester with an aliphatic carboxylic acid. Preferably, the aliphatic carboxylic acid comprises from 4 to 30 and preferably from 8 to 30 carbon atoms. It is preferably chosen from hexanoic acid, heptanoic acid, octanoic acid, 2-ethylhexanoic acid, nonanoic acid, decanoic acid, undecanoic acid, dodecanoic acid, tridecanoic acid, tetradecanoic acid, pentadecanoic acid, hexadecanoic acid, hexyldecanoic acid, heptadecanoic acid, octadecanoic acid, isostearic acid, nonadecanoic acid, eicosanoic acid, isoarachidic acid, octyldodecanoic acid, heneicosanoic acid and docosanoic acid, and mixtures thereof. The aliphatic carboxylic acid is preferably branched. The aliphatic hydroxycarboxylic acid ester is advantageously derived from a hydroxylated aliphatic carboxylic acid containing from 2 to 40 carbon atoms, preferably from 10 to 34 carbon atoms and better still from 12 to 28 carbon atoms, and from 1 to 20 hydroxyl groups, preferably from 1 to 10 hydroxyl groups and better still from 1 to 6 hydroxyl groups. The aliphatic hydroxycarboxylic acid ester is chosen from:

a) partial or total esters of saturated linear monohydroxylated aliphatic monocarboxylic acids;
b) partial or total esters of unsaturated monohydroxylated aliphatic monocarboxylic acids;
c) partial or total esters of saturated monohydroxylated aliphatic polycarboxylic acids;
d) partial or total esters of saturated polyhydroxylated aliphatic polycarboxylic acids;
e) partial or total esters of $C_2$ to $C_{16}$ aliphatic polyols that have reacted with a monohydroxylated or polyhydroxylated aliphatic monocarboxylic or polycarboxylic acid, and mixtures thereof,
esters of a diol dimer and of a diacid dimer, where appropriate esterified on their free alcohol or acid functional group(s) with acid or alcohol radicals, in particular dimer dilinoleate esters; such esters can be chosen in particular from the esters having the following INCI nomenclature: bis-behenyl/isostearyl/phytosteryl dimer dilinoleyl dimer dilinoleate (Plandool G), phytosteryl/isostearyl/cetyl/stearyl/behenyl dimer dilinoleate (Plandool H or Plandool S), and mixtures thereof,
mango butter, such as the product sold under the reference Lipex 203 by AarhusKarlshamn,
hydrogenated soybean oil, hydrogenated coconut oil, hydrogenated rape seed oil, mixtures of hydrogenated vegetable oils such as the mixture of hydrogenated soybean, coconut, palm and rape seed vegetable oil, for example the mixture sold under the reference Akogel® by the company AarhusKarlshamn (INCI name: Hydrogenated Vegetable Oil),
shea butter, in particular the product for which the INCI name is Butyrospermum Parkii Butter, such as the product sold under the reference Sheasoft® by the company AarhusKarlshamn,
and mixtures thereof.

The choice will preferably be made, among the pasty compounds, of bis-behenyl/isostearyl/phytosteryl dimer dilinoleyl dimer dilinoleate, bis-diglyceryl polyacyladipate-2, hydrogenated castor oil, for example Risocast-DA-L sold by Kokyu Alcohol Kogyo, hydrogenated castor oil isostearate, for example Salacos HCIS (V-L) sold by Nisshin Oil, polyvinyl laurate, mango butter, shea butter, hydrogenated soybean oil, hydrogenated coconut oil, hydrogenated rape seed oil, vinylpyrrolidone/eicosene copolymers, or their mixture.

The pasty fatty substance(s) may be present in an amount ranging from 0.5% to 20% by weight and especially from 1% to 10% by weight relative to the total weight of the composition.

A composition used according to the invention may comprise, besides the abovementioned compounds, at least one structuring agent chosen from semi-crystalline polymers, and mixtures thereof.

Semi-Crystalline Polymer

The composition according to the invention may also comprise at least one semi-crystalline polymer, in particular, a semi-crystalline polymer of organic structure whose melting point is greater than or equal to 30° C.

Preferably, the total amount of semi-crystalline polymer(s) represents from 2% to 20% by weight, for example from 3% to 15% by weight and better still from 4% to 10% by weight relative to the total weight of the composition.

For the purposes of the invention, the term "polymers" means compounds comprising at least two repeating units, preferably at least three repeating units and more especially at least ten repeating units.

For the purposes of the invention, the term "semi-crystalline polymer" means polymers comprising a crystallizable portion and an amorphous portion in the backbone and having a first-order reversible change of phase temperature, in particular of melting (solid-liquid transition). The crystallizable portion is either a side chain (or pendent chain) or a block in the backbone.

When the crystallizable portion of the semi-crystalline polymer is a block of the polymer backbone, this crystallizable block has a chemical nature different from that of the amorphous blocks; in this case, the semi-crystalline polymer is a block copolymer, for example of the diblock, triblock or multiblock type. When the crystallizable portion is a chain that is pendent on the backbone, the semi-crystalline polymer may be a homopolymer or a copolymer.

The terms "organic compound" and "having an organic structure" mean compounds containing carbon atoms and hydrogen atoms and optionally heteroatoms such as S, O, N or P, alone or in combination.

The melting point of the semi-crystalline polymer is preferably less than 150° C.

The melting point of the semi-crystalline polymer is preferably greater than or equal to 30° C. and less than 100° C. More preferably, the melting point of the semi-crystalline polymer is preferably greater than or equal to 30° C. and less than 70° C.

The semi-crystalline polymer(s) according to the invention are solid at room temperature (25° C.) and atmospheric pressure (760 mmHg), with a melting point of greater than or equal to 30° C. The melting point values correspond to the melting point measured using a differential scanning calorimeter (DSC), such as the calorimeter sold under the name DSC 30 by the company Mettler, with a temperature rise of 5° C. or 10° C. per minute. (The melting point under consideration is the point corresponding to the temperature of the most endothermic peak of the thermogram).

The semi-crystalline polymer(s) according to the invention preferably have a melting point that is higher than the temperature of the keratinous support intended to receive the said composition, in particular the skin or the lips.

According to the invention, the semi-crystalline polymers are advantageously soluble in the fatty phase, especially to at least 1% by weight, at a temperature that is higher than their melting point. Besides the crystallizable chains or blocks, the blocks of the polymers are amorphous.

For the purposes of the invention, the expression "crystallizable chain or block" means a chain or block which, if it were obtained alone, would change from the amorphous state to the crystalline state reversibly, depending on whether one is above or below the melting point. For the purposes of the invention, a "chain" is a group of atoms, which are pendent or lateral relative to the polymer backbone. A "block" is a group of atoms belonging to the backbone, this group constituting one of the repeating units of the polymer.

According to one preferred embodiment, the semi-crystalline polymer is chosen from:
homopolymers and copolymers comprising units resulting from the polymerization of one or more monomers bearing crystallizable hydrophobic side chain(s),
polymers bearing in the backbone at least one crystallizable block,
polycondensates of aliphatic or aromatic or aliphatic/aromatic polyester type
copolymers of ethylene and propylene prepared via metallocene catalysis.

The semi-crystalline polymers that may be used in the invention may in particular be chosen from:
block copolymers of polyolefins of controlled crystallization, whose monomers are described in EP-A-0 951 897,
polycondensates, especially of aliphatic or aromatic or aliphatic/aromatic polyester type,
copolymers of ethylene and propylene prepared via metallocene catalysis,
homopolymers or copolymers bearing at least one crystallizable side chain and homopolymers or copolymers bearing at least one crystallizable block in the backbone, for instance those described in document U.S. Pat. No. 5,156,911,
homopolymers or copolymers bearing at least one crystallizable side chain, in particular bearing fluoro group(s), such as those described in document WO-A-01/19333,
and mixtures thereof.

Examples of semi-crystalline polymers that may be mentioned include those described in patent application WO 2010/010 301.

According to one preferred embodiment, the semi-crystalline polymer is chosen from homopolymers and copolymers comprising units resulting from the polymerization of one or more monomers bearing crystallizable hydrophobic side chains, and is preferably chosen from poly($C_{10-30}$)alkyl acrylates, preferably such as polystearyl acrylate, sold especially under the reference Intelimer IPA 13-1 by the company Air Products & Chemicals, and also polybehenyl acrylate, sold especially under the reference Intelimer IPA 13-6 by the company Air Products & Chemicals.

Aqueous Phase

As stated hereinabove, a composition according to the invention comprises at least 20% of water.

The water may be present in a total content ranging from 20% to 95% by weight. Preferably, the water is present in a content ranging from 30% to 90% by weight, relative to the total weight of the composition.

More preferably, the water is present in a content ranging from 40% to 85% by weight relative to the total weight of the composition.

Preferably, the composition according to the invention comprises at least 30% by weight of water, preferably at least 40% by weight and preferably at least 50% by weight of water, relative to the total weight of the composition.

The composition in accordance with the invention may comprise, besides water, at least one water-soluble solvent.

The aqueous phase may constitute the continuous phase of the composition.

The term "composition with an aqueous continuous phase" means that the composition has a conductivity, measured at 25° C., of greater than or equal to 23 µS/cm (microSiemens/cm), the conductivity being measured, for example, using an MPC227 conductimeter from Mettler Toledo and an Inlab730 conductivity measuring cell. The measuring cell is immersed in the composition so as to remove the air bubbles that might be formed between the two electrodes of the cell. The conductivity reading is taken once the conductimeter value has stabilized. A mean is determined on at least three successive measurements.

In the present invention, the term "water-soluble solvent" denotes a compound that is liquid at room temperature and water-miscible (miscibility with water of greater than 50% by weight at 25° C. and atmospheric pressure).

The water-soluble solvents which can be used in the compositions according to the invention can in addition be volatile.

Among the water-soluble solvents that may be used in the compositions in accordance with the invention, mention may be made especially of lower monoalcohols containing from 1 to 5 carbon atoms, such as ethanol and isopropanol, glycols containing from 2 to 8 carbon atoms, such as ethylene glycol, propylene glycol, 1,3-butylene glycol and dipropylene glycol, $C_3$ and $C_4$ ketones and $C_2$-$C_4$ aldehydes.

The aqueous phase (water and optionally the water-miscible solvent) may be present in the composition in a content ranging from 20% to 95% by weight and preferably ranging from 30% to 90% by weight relative to the total weight of the composition. In a particularly preferred manner, the aqueous phase (water and optionally the water-miscible solvent) is present in the composition in a content ranging from 40% to 85% by weight, relative to the total weight of the composition.

The aqueous phase according to the invention may also comprise at least one hydrophilic film-forming polymer and/or at least one hydrophilic thickener and/or at least one surfactant. However, the content of aqueous phase indicated previously does not include the contents of each of the abovementioned compounds.

According to one particularly preferred embodiment, the composition according to the invention is an oil-in-water emulsion.

Surfactant:

The composition according to the invention comprises at least one surfactant, preferably non-silicone. Preferably, the composition is such that the surfactant is present in a content ranging from 0.1% to 20% by weight relative to the total weight of the composition.

The composition according to the invention may, of course, comprise several surfactants.

The composition according to the invention comprises an emulsifying system comprising at least one surfactant, especially in a content ranging from 0.1% to 20% by weight, or even 0.5% to 15% by weight and preferably ranging from 1% to 10% by weight relative to the total weight of the composition. Preferably, the total content of surfactants(s) is between 0.1% and 20% by weight and preferably between 0.5% and 15% by weight relative to the total weight of the composition.

Advantageously, it is present in a content such that the non-volatile oils/content of surfactant(s) weight ratio is between 1 and 40 and preferably between 3 and 35.

Preferably, they are present in a total content of non-volatile oils/content of surfactant(s) weight ratio of between 4 and 25.

An emulsifying surfactant appropriately chosen to obtain an oil-in-water emulsion is preferably used.

In particular, an emulsifying surfactant having at 25° C. an HLB balance (hydrophilic-lipophilic balance) within the Griffin sense of greater than or equal to 8 may be used.

An emulsifying surfactant having at 25° C. an HLB balance (hydrophilic-lipophilic balance) within the Griffin sense of less than 8 may also be used.

The Griffin HLB value is defined in J. Soc. Cosm. Chem. 1954 (volume 5), pages 249-256.

These surfactants may be chosen from nonionic, anionic, cationic and amphoteric surfactants, and mixtures thereof. Reference may be made to Kirk-Othmer's Encyclopedia of Chemical Technology, Volume 22, pp. 333-432, 3rd Edition, 1979, Wiley, for the definition of the emulsifying properties and functions of surfactants, in particular pp. 347-377 of this reference, for the anionic, amphoteric and nonionic surfactants.

According to a first embodiment, the composition comprises at least one hydrocarbon-based surfactant.

Examples of hydrocarbon-based surfactants that are suitable for use in the invention are described below.

Nonionic surfactants Preferably, the composition according to the invention comprises at least one nonionic surfactant.

The nonionic surfactants may be chosen especially from alkyl and polyalkyl esters of poly(ethylene oxide), oxyalkylenated alcohols, alkyl and polyalkyl ethers of poly(ethylene oxide), optionally polyoxyethylenated alkyl and polyalkyl esters of sorbitan, optionally polyoxyethylenated alkyl and polyalkyl ethers of sorbitan, alkyl and polyalkyl glycosides or polyglycosides, in particular alkyl and polyalkyl glucosides or polyglucosides, alkyl and polyalkyl esters of sucrose, optionally polyoxyethylenated alkyl and polyalkyl esters of glycerol, optionally polyoxyethylenated alkyl and polyalkyl ethers of glycerol, gemini surfactants, cetyl alcohol and stearyl alcohol, and mixtures thereof.

1) Alkyl and polyalkyl esters of poly(ethylene oxide) that are preferably used include those with a number of ethylene oxide (EO) units ranging from 2 to 200. Examples that may be mentioned include stearate 40 EO, stearate 50 EO, stearate 100 EO, laurate 20 EO, laurate 40 EO and distearate 150 EO.

2) Alkyl and polyalkyl ethers of poly(ethylene oxide) that are preferably used include those with a number of ethylene oxide (EO) units ranging from 2 to 200. Examples that may be mentioned include cetyl ether 23 EO, oleyl ether 50 EO, phytosterol 30 EO, steareth 40, steareth 100 and beheneth 100.

3) As oxyalkylenated alcohols, which are in particular oxyethylenated and/or oxypropylenated, use is preferably made of those that can comprise from 1 to 150 oxyethylene and/or oxypropylene units, in particular containing from 20 to 100 oxyethylene units, in particular ethoxylated fatty alcohols, especially of $C_8$-$C_{24}$ and preferably of $C_{12}$-$C_{18}$, which may or may not be ethoxylated, for instance stearyl alcohol ethoxylated with 20 oxyethylene units (CTFA name Steareth-20), for instance Brij 78 sold by the company Uniqema, cetearyl alcohol ethoxylated with 30 oxyethylene units (CTFA name Ceteareth-30), and the mixture of $C_{12}$-$C_{15}$ fatty alcohols comprising 7 oxyethylene units (CTFA name $C_{12}$-$C_{15}$ Pareth-7), for instance the product sold under the name Neodol 25-7® by Shell Chemicals; or in particular oxyalkylenated (oxyethylenated and/or oxypropylenated) alcohols containing from 1 to 15 oxyethylene and/or oxypropylene units, in particular ethoxylated $C_8$-$C_{24}$ and preferably $C_{12}$-$C_{18}$ fatty alcohols, such as stearyl alcohol ethoxylated with 2 oxyethylene units (CTFA name Steareth-2), for instance Brij 72 sold by the company Uniqema;

4) Optionally polyoxyethylenated alkyl and polyalkyl esters of sorbitan that are preferably used include those with a number of ethylene oxide (EO) units ranging from 0 to 100. Examples that may be mentioned include sorbitan laurate 4 or 20 EO, in particular polysorbate 20 (or polyoxyethylene (20) sorbitan monolaurate) such as the product Tween 20 sold by the company Uniqema, sorbitan palmitate 20 EO, sorbitan stearate 20 EO, sorbitan oleate 20 EO, or the Cremophor products (RH 40, RH 60, etc.) from BASF. Mention may also be made of the mixture of sorbitan stearate and sucrose cocoate (sold under the name Arlacel 2121U-FL from Croda).

5) Optionally polyoxyethylenated alkyl and polyalkyl ethers of sorbitan that are preferably used include those with a number of ethylene oxide (EO) units ranging from 0 to 100.

6) Alkyl and polyalkyl glucosides or polyglucosides that are preferably used include those containing an alkyl group comprising from 6 to 30 carbon atoms and preferably from 6 to 18 or even from 8 to 16 carbon atoms, and containing a glucoside group preferably comprising from 1 to 5 and especially 1, 2 or 3 glucoside units. The alkylpolyglucosides may be chosen, for example, from decylglucoside (alkyl-$C_9/C_{11}$-polyglucoside (1.4)), for instance the product sold under the name Mydol 10® by the company Kao Chemicals or the product sold under the name Plantacare 2000 UP® by the company Henkel and the product sold under the name Oramix NS 10® by the company SEPPIC; caprylyl/capryl glucoside, for instance the product sold under the name Plantacare KE 3711® by the company Cognis or Oramix CG 110® by the company SEPPIC; laurylglucoside, for instance the product sold under the name Plantacare 1200 UP® by the company Henkel or Plantaren 1200 N® by the company Henkel; cocoglucoside, for instance the product sold under the name Plantacare 818 UP® by the company Henkel; caprylylglucoside, for instance the product sold under the name Plantacare 810 UP® by the company Cognis; the mixture of arachidyl glucoside and behenyl alcohol and arachidyl alcohol, whose INCI name is Arachidyl alcohol (and) behenyl alcohol (and) arachidyl glucoside, sold under the name Montanov 202 by the company SEPPIC; and mixtures thereof. More generally, the surfactants of alkylpolyglycoside type are defined more specifically hereinbelow.

7) As alkyl and polyalkyl esters of sucrose, in particular C12-C26 alkyl esters, examples that may be mentioned include sucrose stearate, sold especially under the name Tegosoft PSE 141 G by the company Evonik Goldschmidt, the mixture of sorbitan stearate and sucrose cocoate (sold under the name Arlatone Arlacel 2121 U-FL from Croda), Crodesta F150, the sucrose monolaurate sold under the name Crodesta SL 40, and the products sold by Ryoto Sugar Ester, for instance the sucrose palmitate sold under the references Ryoto Sugar Ester P 1670, Ryoto Sugar Ester LWA 1695 and Ryoto Sugar Ester 01570.

8) Optionally polyoxyethylenated alkyl and polyalkyl esters of glycerol that are preferably used include those with a number of ethylene oxide (EO) units ranging from 0 to 100 and a number of glycerol units ranging from 1 to 30. Examples that may be mentioned include PEG-150 distearate sold under the reference Kessco PEG 6000 DS by the company Italmatch Chemicals Arese, hexaglyceryl monolaurate and PEG-30 glyceryl stearate.

9) Optionally polyoxyethylenated alkyl and polyalkyl ethers of glycerol that are preferably used include those with a number of ethylene oxide (EO) units ranging from 0 to 100 and a number of glycerol units ranging from 1 to 30. Examples that may be mentioned include Nikkol batyl alcohol 100 and Nikkol chimyl alcohol 100;

10) cetyl alcohol and stearyl alcohol;

11) The gemini surfactants of formula (I):

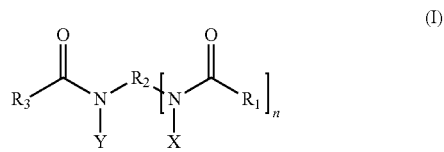

in which:
R$_1$ and R$_3$ denote, independently of one another, an alkyl radical containing from 1 to 25 carbon atoms;
R$_2$ denotes a spacer consisting of a linear or branched alkylene chain containing from 1 to 12 carbon atoms;
X and Y denote, independently of each other, a group —$(C_2H_4O)_a$—$(C_3H_6O)_b$Z, where:
Z denotes a hydrogen atom or a radical —CH$_2$—COOM, —SO$_3$M, —P(O)(OM)$_2$, —C$_2$H$_4$—SO$_3$M, —C$_3$H$_6$—SO$_3$M or —CH$_2$(CHOH)$_4$CH$_2$OH, where M and M' represent H or an alkali metal or alkaline-earth metal or ammonium or alkanolammonium ion,
a ranges from 0 to 15,
b ranges from 0 to 10, and
the sum of a+b ranges from 1 to 25; and
−n ranges from 1 to 10, for example the gemini surfactant as a mixture with other surfactants in the form of the products sold by Sasol under the Ceralution® names, in particular the following products: •Ceralution® H: Behenyl Alcohol, Glyceryl Stearate, Glyceryl Stearate Citrate and Sodium Dicocoylethylenediamine PEG-15 Sulfate, •Ceralution® F: Sodium Lauroyl Lactylate and Sodium Dicocoylethylenediamine PEG-15 Sulfate, •Ceralution® C: Aqua, Capric/Caprylic triglyceride, Glycerin, Ceteareth-25, Sodium Dicocoylethylenediamine PEG-15 Sulfate, Sodium Lauroyl Lactylate, Behenyl Alcohol, Glyceryl Stearate, Glyceryl Stearate Citrate, Gum Arabic, Xanthan Gum, Phenoxyethanol, Methylparaben, Ethylparaben, Butylparaben, Isobutylparaben (INCI names)

12) and mixtures thereof.

Preferably, the nonionic surfactant is chosen from alkyl and polyalkyl glucosides or polyglucosides, preferably those containing an alkyl group comprising from 6 to 30 carbon atoms, preferably from 6 to 18 or even from 8 to 16 carbon atoms, and containing a glucoside group preferably comprising from 1 to 5 and especially from 1.2 to 3 glucoside units.

The alkylpolyglucosides may be chosen, for example, from decyl glucoside ($C_9/C_{11}$-alkylpolyglucoside (1.4)); caprylyl/capryl glucoside; lauryl glucoside; cocoyl glucoside; caprylyl glucoside; the mixture of arachidyl glucoside and behenyl alcohol and arachidyl alcohol; and mixtures thereof.

The nonionic surfactant is, particularly preferably, a mixture of arachidyl glucoside, behenyl alcohol and arachidyl alcohol. Preferably, the nonionic surfactant is the compound whose INCI name is Arachidyl alcohol (and) behenyl alcohol (and) arachidyl glucoside, sold especially under the name Montanov 202 by the company SEPPIC.

Preferably, the composition according to the invention comprises the alkyl or polyalkyl glucoside or polyglucoside nonionic surfactant in a content ranging from 0.1% to 20% by weight, or even 0.5% to 15% by weight and preferably ranging from 1% to 10% by weight relative to the total weight of the composition.

Anionic Surfactants

The anionic surfactants may be chosen from alkyl ether sulfates, carboxylates, amino acid derivatives, sulfonates, isethionates, taurates, sulfosuccinates, alkylsulfoacetates, phosphates and alkyl phosphates, polypeptides, metal salts of $C_{10}$-$C_{30}$ and especially $C_{16}$-$C_{25}$ fatty acids, in particular metal stearates and behenates, and mixtures thereof.

1) Examples of alkyl ether sulfates that may be mentioned include sodium lauryl ether sulfate (70/30 C12-14) (2.2 EO) sold under the names Sipon AOS225 or Texapon N702 by the company Henkel, ammonium lauryl ether sulfate (70/30 C12-14) (3 EO) sold under the name Sipon LEA 370 by the company Henkel, ammonium ($C_{12}$-$C_{14}$) alkyl ether (9 EO) sulfate sold under the name Rhodapex AB/20 by the company Rhodia Chimie, and the mixture of sodium magnesium lauryl oleyl ether sulfate sold under the name Empicol BSD 52 by the company Albright & Wilson.

2) Examples of carboxylates that may be mentioned include salts (for example alkali metal salts) of N-acylamino acids, glycol carboxylates, amido ether carboxylates (AEC) and polyoxyethylenated carboxylic acid salts.

The surfactant of glycol carboxylate type may be chosen from alkyl glycol carboxylates or 2-(2-hydroxyalkyloxy acetate), salts thereof and mixtures thereof. These alkyl glycol carboxylics comprise a linear or branched, saturated or unsaturated aliphatic and/or aromatic alkyl chain containing from 8 to 18 carbon atoms. These carboxylics may be neutralized with mineral bases such as potassium hydroxide or sodium hydroxide.

Examples of surfactants of glycol carboxylic type that may be mentioned include sodium lauryl glycol carboxylate or sodium 2-(2-hydroxyalkyloxy acetate) such as the product sold under the name Beaulight Shaa® by the company Sanyo, Beaulight LCA-25N® or the corresponding acid from Beaulight Shaa (Acid form)®.

An example of an amido ether carboxylate (AEC) that may be mentioned is sodium lauryl amido ether carboxylate (3 EO) sold under the name Akypo Foam 30® by the company Kao Chemicals.

Examples of polyoxyethylenated carboxylic acid salts that may be mentioned include oxyethylenated (6 EO) sodium lauryl ether carboxylate (65/25/10 $C_{12\text{-}14\text{-}16}$) sold under the name Akypo Soft 45 NV® by the company Kao Chemicals, polyoxyethylenated and carboxymethylated fatty acids of olive oil origin sold under the name Olivem 400® by the company Biologia e Tecnologia, and oxyethylenated (6 EO) sodium tridecyl ether carboxylate sold under the name Nikkol ECTD-6 NEX® by the company Nikkol.

3) Amino acid derivatives that may especially be mentioned include alkali metal salts of amino acids, such as:
sarcosinates, for instance the sodium lauroyl sarcosinate sold under the name Sarkosyl NL 97® by the company Ciba or sold under the name Oramix L30® by the company SEPPIC, sodium myristoyl sarcosinate sold under the name Nikkol Sarcosinate MN® by the company Nikkol, and sodium palmitoyl sarcosinate sold under the name Nikkol Sarcosinate PN® by the company Nikkol;
alaninates, for instance sodium N-lauroyl N-methyl amidopropionate sold under the name Sodium Nikkol Alaninate LN30® by the company Nikkol, or sold under the name Alanone ALE® by the company Kawaken, and triethanolamine N-lauroyl N-methyl alanine sold under the name Alanone Alta® by the company Kawaken;
glutamates, for instance triethanolamine monococoyl glutamate sold under the name Acylglutamate CT-12® by the company Ajinomoto, or triethanolamine lauroyl glutamate sold under the name Acylglutamate LT-12® by the company Ajinomoto;
and mixtures thereof, for instance the mixture of Palmitoyl proline (and) sodium palmitoyl sarcosinate (and) magnesium palmitoyl glutamate, sold especially under the reference Sepifeel One by the company SEPPIC.

The glutamic acid salts and/or derivatives are described more specifically hereinbelow.
aspartates, for instance the mixture of triethanolamine N-lauroyl aspartate and of triethanolamine N-myristoyl aspartate, sold under the name Asparack® by the company Mitsubishi;
glycine derivatives (glycinates), for instance the sodium N-cocoyl glycinate sold under the names Amilite GCS-12® and Amilite GCK 12 by the company Ajinomoto;
citrates, such as the oxyethylenated (9 mol) citric monoester of cocoyl alcohols sold under the name Witconol EC 1129 by the company Goldschmidt;
galacturonates, such as the sodium dodecyl-D-galactoside uronate sold by the company Soliance.

4) Examples of sulfonates that may be mentioned include α-olefin sulfonates, for instance the sodium α-olefin sulfonate ($C_{14\text{-}16}$) sold under the name Bio-Terge AS-40® by the company Stepan, sold under the names Witconate AOS Protégé® and Sulframine AOS PH 12® by the company Witco or sold under the name Bio-Terge AS-40 CG® by the company Stepan, the sodium secondary olefin sulfonate sold under the name Hostapur SAS 30® by the company Clariant.

5) Isethionates that may be mentioned include acylisethionates, for instance sodium cocoylisethionate, such as the product sold under the name Jordapon CI P® by the company Jordan.

6) Taurates that may be mentioned include the sodium salt of palm kernel oil methyltaurate sold under the name Hostapon CT Pate® by the company Clariant; N-acyl N-methyltaurates, for instance the sodium N-cocoyl N-methyltaurate sold under the name Hostapon LT-SF® by the company Clariant or sold under the name Nikkol CMT-30-T® by the company Nikkol, and the sodium palmitoyl methyltaurate sold under the name Nikkol PMT® by the company Nikkol.

7) Examples of sulfosuccinates that may be mentioned include the oxyethylenated (3 EO) lauryl alcohol monosulfosuccinate (70/30 $C_{12}$/$C_{14}$) sold under the names Setacin 103 Special® and Rewopol SB-FA 30 K 4® by the company Witco, the disodium salt of a $C_{12}$-$C_{14}$ alkyl hemisulfosuccinate, sold under the name Setacin F Special Paste® by the company Zschimmer Schwarz, the oxyethylenated (2 EO) disodium oleamidosulfosuccinate sold under the name Standapol SH 135® by the company Henkel, the oxyethylenated (5 EO) laurylamide monosulfosuccinate sold under the name Lebon A-5000® by the company Sanyo, the oxyethylenated (10 EO) disodium salt of lauryl citrate monosulfosuccinate sold under the name Rewopol SB CS 50® by the company Witco, and the ricinoleic monoethanolamide monosulfosuccinate sold under the name Rewoderm S 1333® by the company Witco. Polydimethylsiloxane sulfosuccinates may also be used, such as disodium PEG-12 dimethicone sulfosuccinate sold under the name Mackanate-DC30 by the company MacIntyre.

8) Examples of alkyl sulfoacetates that may be mentioned include the mixture of sodium lauryl sulfoacetate and disodium lauryl ether sulfosuccinate, sold under the name Stepan Mild LSB by the company Stepan.

9) Examples of phosphates and alkyl phosphates that may be mentioned include monoalkyl phosphates and dialkyl phosphates, such as the lauryl monophosphate sold under the name MAP 20® by the company Kao Chemicals, the potassium salt of dodecylphosphoric acid, mixture of monoester and diester (predominantly diester) sold under the name Crafol AP-31® by the company Cognis, the mixture of octylphosphoric acid monoester and diester sold under the name Crafol AP-20® by the company Cognis, the mixture of ethoxylated (7 mol of EO) phosphoric acid diester of 2-butyloctanol, sold under the name Isofol 12 7 EO-Phosphate Ester® by the company Condea, the potassium or triethanolamine salt of mono($C_{12}$-$C_{13}$)alkyl phosphate sold under the references Arlatone MAP 230K-40® and Arlatone MAP 230T-60® by the company Uniqema, the potassium lauryl phosphate sold under the name Dermalcare MAP XC-99/09® by the company Rhodia Chimie, and the potassium cetyl phosphate sold under the name Arlatone MAP 160K by the company Uniqema.

10) The polypeptides are obtained, for example, by condensation of a fatty chain onto amino acids from cereals and especially from wheat and oat. Examples of polypeptides that may be mentioned include the potassium salt of hydrolysed lauroyl wheat protein, sold under the name Aminofoam W OR by the company Croda, the triethanolamine salt of hydrolysed cocoyl soybean protein, sold under the name May-Tein SY by the company Maybrook, the sodium salt of lauroyl oat amino acids, sold under the name Proteol Oat by the company SEPPIC, collagen hydrolysate grafted onto coconut fatty acid, sold under the name Geliderm 3000 by the company Deutsche Gelatine, and soybean proteins acylated with hydrogenated coconut acids, sold under the name Proteol VS 22 by the company SEPPIC.

11) Metal salts of $C_{10}$-$C_{30}$ and preferably $C_{16}$-$C_{25}$ fatty acids that may be mentioned in particular include metal behenates, such as sodium behenate, and metal stearates, such as sodium stearate, sold especially under the reference Vegetable sodium stearate 35/65 from FACI, and potassium stearate, and also polyhydroxy stearates;

12) and mixtures thereof.

Cationic Surfactants

The cationic surfactants may be chosen from:
alkylimidazolidiniums such as isostearylethylimidonium ethosulfate,
ammonium salts such as ($C_{12-30}$ alkyl)tri($C_{1-4}$ alkyl)ammonium halides, for instance N,N,N-trimethyl-1-docosanaminium chloride (or behentrimonium chloride).

The compositions according to the invention may also contain one or more amphoteric surfactants, for instance N-acylamino acids such as N-alkyl aminoacetates and disodium cocoamphodiacetate, and amine oxides such as stearamine oxide, or alternatively silicone surfactants, for instance dimethicone copolyol phosphates such as the product sold under the name Pecosil PS 100® by the company Phoenix Chemical.

According to a second embodiment, the composition comprises at least one silicone surfactant. Examples that may be mentioned include:

a) nonionic surfactants with an HLB of greater than or equal to 8 at 25° C., used alone or as a mixture; mention may be made especially of:
dimethicone copolyol, such as the product sold under the name Q2-5220® by the company Dow Corning;
dimethicone copolyol benzoate, such as the product sold under the names Finsolv SLB 101® and 201® by the company Fintex;

b) nonionic surfactants with an HLB of greater than or equal to 8 at 25° C., used alone or as a mixture; mention may be made especially of:
the mixture of cyclomethicone/dimethicone copolyol sold under the name Q2-3225C® by the company Dow Corning.

Preferably, the composition according to the invention comprises at least one nonionic or anionic surfactant.

Preferably, the composition according to the invention comprises at least one surfactant chosen from:
amino acid derivatives and in particular glutamates, such as the mixture of Palmitoylproline (and) sodium palmitoyl sarcosinate (and) magnesium palmitoyl glutamate sold especially under the reference Sepifeel One by the company SEPPIC, and/or
alkyl and polyalkyl esters of sucrose, in particular $C_{12}$-$C_{26}$ alkyl esters: examples that may be mentioned include sucrose stearate, sold especially under the name Tegosoft PSE 141 G by the company Evonik Goldschmidt, and/or the mixture of sorbitan stearate and sucrose cocoate (sold under the name Arlacel 2121U-FL from Croda);
alkyl and polyalkyl glucosides or polyglucosides, preferably those containing an alkyl group comprising from 6 to 30 carbon atoms, preferably from 6 to 18 or even from 8 to 16 carbon atoms, and containing a glucoside group preferably comprising from 1 to 5 and especially from 1, 2 to 3 glucoside units, preferably the alkylpolyglucosides chosen from decyl glucoside ($C_9/C_{11}$-alkylpolyglucoside (1.4)); caprylyl/capryl glucoside; lauryl glucoside; cocoyl glucoside; caprylyl glucoside; and the mixture of arachidyl glucoside and behenyl alcohol and arachidyl alcohol, whose INCI name is Arachidyl alcohol (and) behenyl alcohol (and) arachidyl glucoside,
and mixtures thereof.

Preferably, the surfactant is chosen from: (1) amino acid derivatives and in particular glutamates, preferably such as the mixture of Palmitoylproline (and) sodium palmitoyl sarcosinate (and) magnesium palmitoyl glutamate, and/or (2) alkyl and polyalkyl esters of sucrose, in particular $C_{12}$-$C_{26}$ alkyl esters, preferably such as sucrose stearate, and/or such as the mixture of sorbitan stearate and sucrose cocoate; and mixtures thereof.

Hydrophilic Gelling Polymers

The composition according to the invention may additionally comprise a hydrophilic gelling agent, preferably chosen from associative polymers.

Preferably, the composition is such that the hydrophilic gelling agent (preferably an associative polymer), if present, is in a content ranging from 0.1% to 10% by weight, relative to the total weight of the composition.

For the purposes of the present patent application, the term "polymer for gelling the aqueous phase" means a polymer that is capable of gelling the aqueous phase of the compositions according to the invention.

The gelling polymer that may be used according to the invention may especially be characterized by its capacity to form in water, beyond a certain concentration C*, a gel characterized by oscillatory rheology ($\mu$=1 Hz) by a flow threshold $\tau_c$ at least equal to 10 Pa. This concentration C* may vary widely according to the nature of the gelling polymer under consideration.

By way of illustration, this concentration is between 1% and 2% by weight for an acrylamide/sodium acrylamido-2-methylpropanesulfonate copolymer as an inverse emulsion at 40% in polysorbate 80/I-C16, for instance the product sold under the name Simulgel 600 by the company SEPPIC, and is about 0.5% by weight for an AMPS/ethoxylated (25 EO) cetearyl methacrylate copolymer crosslinked with trimethylolpropane triacrylate (TMPTA) of the type such as Aristoflex HMS.

The gelling polymer may be present in the composition in an amount that is sufficient to adjust the stiffness modulus G* (1 Hz, 25° C.) of the composition to a value greater than or equal to 10 000 Pa and especially ranging from 10 000 Pa to 100 000 Pa. The method for measuring the stiffness modulus G* (1 Hz, 25° C.) of the composition is described in greater detail hereinbelow.

The gelling polymer is a hydrophilic polymer and is thus present in the aqueous phase of the composition.

More particularly, this gelling polymer may be chosen from:
  acrylic or methacrylic acid homopolymers or copolymers or salts and esters thereof and in particular the products sold under the names Versicol F or Versicol K by the company Allied Colloid, Ultrahold 8 by the company Ciba-Geigy, and polyacrylic acids of Synthalen K type, and salts, especially sodium salts, of polyacrylic acids (corresponding to the INCI name sodium acrylate copolymer) and more particularly a crosslinked sodium polyacrylate (corresponding to the INCI name sodium acrylate copolymer (and) caprylic/capric triglycerides) sold under the name Luvigel EM by the company,
  copolymers of acrylic acid and of acrylamide sold in the form of the sodium salt thereof under the names Reten by the company Hercules, the sodium polymethacrylate sold under the name Darvan No. 7 by the company Vanderbilt, and the sodium salts of polyhydroxycarboxylic acids sold under the name Hydagen F by the company Henkel,
  polyacrylic acid/alkyl acrylate copolymers, preferably modified or unmodified carboxyvinyl polymers; the copolymers most particularly preferred according to the present invention are acrylate/$C_{10}$-$C_{30}$-alkylacrylate copolymers (INCI name: Acrylates/$C_{10-30}$ Alkyl acrylate Crosspolymer) such as the products sold by the company Lubrizol under the trade names Pemulen TR1, Pemulen TR2, Carbopol 1382 and Carbopol EDT 2020, and even more preferentially Pemulen TR-2;
  AMPS (polyacrylamidomethylpropanesulfonic acid partially neutralized with aqueous ammonia and highly crosslinked) sold by the company Clariant,
  AMPS/acrylamide copolymers of Sepigel or Simulgel type sold by the company SEPPIC, and
  polyoxyethylenated AMPS/alkyl methacrylate copolymers (crosslinked or non-crosslinked) of the type such as Aristoflex HMS sold by the company Clariant,
  and mixtures thereof.
Other examples of hydrophilic gelling polymers that may be mentioned include:
  anionic, cationic, amphoteric or nonionic chitin or chitosan polymers;
  cellulose polymers, other than alkylcellulose, chosen from hydroxyethylcellulose, hydroxypropylcellulose, hydroxy methylcellulose, ethylhydroxyethylcellulose and carboxymethylcellulose, and also quaternized cellulose derivatives;
  vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol;
  optionally modified polymers of natural origin, such as: galactomannans and derivatives thereof, such as konjac gum, gellan gum, locust bean gum, fenugreek gum, karaya gum, gum tragacanth, gum arabic, acacia gum, guar gum, hydroxypropyl guar, hydroxypropyl guar modified with sodium methylcarboxylate groups (Jaguar XC97-1, Rhodia), hydroxypropyltrimethylammonium guar chloride, and xanthan derivatives;
    alginates and carrageenans;
    glycoaminoglycans, hyaluronic acid and derivatives thereof;
    deoxyribonucleic acid;
    mucopolysaccharides such as hyaluronic acid and chondroitin sulfates, and mixtures thereof.

According to one preferred embodiment, the gelling polymer is chosen from acrylic or methacrylic acid homopolymers or copolymers or salts and esters thereof, polyacrylic acids and polyacrylic acid salts, or mixtures thereof.

According to one preferred embodiment, the gelling polymer is a sodium salt of polyacrylic acid, especially a crosslinked sodium polyacrylate.

According to one particularly preferred embodiment, the gelling agent is chosen from associative polymers.

For the purposes of the present invention, the term "associative polymer" means any amphiphilic polymer comprising in its structure at least one fatty chain and at least one hydrophilic portion. The associative polymers in accordance with the present invention may be anionic, cationic, nonionic or amphoteric.

Associative Anionic Polymers

Among the associative anionic polymers that may be mentioned are those comprising at least one hydrophilic unit, and at least one fatty-chain allyl ether unit, more particularly those whose hydrophilic unit is formed by an unsaturated ethylenic anionic monomer, advantageously by a vinylcarboxylic acid and most particularly by an acrylic acid or a methacrylic acid or mixtures thereof, and whose fatty-chain allyl ether unit corresponds to the monomer of formula (I) below:

$$CH_2=C(R')CH_2O\ B_nR \qquad (I)$$

in which R' denotes H or $CH_3$, B denotes the ethylenoxy radical, n is zero or denotes an integer ranging from 1 to 100, R denotes a hydrocarbon-based radical chosen from alkyl, arylalkyl, aryl, alkylaryl and cycloalkyl radicals, comprising from 8 to 30 carbon atoms, preferably 10 to 24 and even more particularly from 12 to 18 carbon atoms.

Anionic amphiphilic polymers of this type are described and prepared, according to an emulsion polymerization process, in patent EP-0 216 479.

Among the associative anionic polymers that may also be mentioned are maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name Performa V 1608 by the company Newphase Technologies.

Among the associative anionic polymers, use may be made, according to one preferred embodiment, of copolymers comprising among their monomers an α,β-monoethylenically unsaturated carboxylic acid and an ester of an α,β-monoethylenically unsaturated carboxylic acid and of an oxyalkylenated fatty alcohol.

Preferentially, these compounds also comprise as monomer an ester of an α,β-monoethylenically unsaturated carboxylic acid and of a $C_1$-$C_4$ alcohol.

Examples of compounds of this type that may be mentioned include Aculyn 22® sold by the company Rohm & Haas, which is a methacrylic acid/ethyl acrylate/oxyalkylenated stearyl methacrylate (comprising 20 OE units) terpolymer or Aculyn 28 (methacrylic acid/ethyl acrylate/oxyethylenated behenyl methacrylate (25 OE) terpolymer).

Examples of associative anionic polymers that may also be mentioned include anionic polymers comprising at least one hydrophilic unit of unsaturated olefinic carboxylic acid type, and at least one hydrophobic unit exclusively of the type such as a ($C_{10}$-$C_{30}$) alkyl ester of an unsaturated carboxylic acid. Examples that may be mentioned include the anionic polymers described and prepared according to patents U.S. Pat. Nos. 3,915,921 and 4,509,949.

Cationic Associative Polymers

Cationic associative polymers that may be mentioned include quaternized cellulose derivatives and polyacrylates bearing amine side groups.

The quaternized cellulose derivatives are, in particular:
quaternized celluloses modified with groups comprising at least one fatty chain, such as alkyl, arylalkyl or alkylaryl groups comprising at least 8 carbon atoms, or mixtures thereof,
quaternized hydroxyethylcelluloses modified with groups comprising at least one fatty chain, such as alkyl, arylalkyl or alkylaryl groups comprising at least 8 carbon atoms, or mixtures thereof.

The polyacrylates bearing quaternized or non-quaternized amine side groups contain, for example, hydrophobic groups of the type such as steareth-20 (polyoxyethylenated (20) stearyl alcohol).

The alkyl radicals borne by the above quaternized celluloses or hydroxyethylcelluloses preferably comprise from 8 to 30 carbon atoms. The aryl radicals preferably denote phenyl, benzyl, naphthyl or anthryl groups.

Examples of quaternized alkylhydroxyethylcelluloses containing $C_8$-$C_{30}$ fatty chains that may be indicated include the products Quatrisoft LM 200, Quatrisoft LM-X 529-18-A, Quatrisoft LM-X 529-18B ($C_{12}$ alkyl) and Quatrisoft LM-X 529-8 ($C_{18}$ alkyl) sold by the company Amerchol and the products Crodacel QM, Crodacel QL ($C_{12}$ alkyl) and Crodacel QS ($C_{18}$ alkyl) sold by the company Croda.

Examples of polyacrylates bearing amino side chains that may be mentioned are the polymers 8781-121B or 9492-103 from the company National Starch.

Nonionic Associative Polymers

The nonionic associative polymers may be chosen from:
celluloses modified with groups comprising at least one fatty chain, for instance hydroxyethylcelluloses modified with groups comprising at least one fatty chain, such as alkyl groups, especially of $C_8$-$C_{22}$, arylalkyl and alkylaryl groups, such as Natrosol Plus Grade 330 CS ($C_{16}$ alkyls) sold by the company Aqualon,
celluloses modified with alkylphenyl polyalkylene glycol ether groups, such as the product Amercell Polymer HM-1500 (nonylphenyl polyethylene glycol (15) ether) sold by the company Amerchol,
guars such as hydroxypropyl guar, modified with groups comprising at least one fatty chain such as an alkyl chain,
copolymers of vinylpyrrolidone and of fatty-chain hydrophobic monomers,
copolymers of $C_1$-$C_6$ alkyl methacrylates or acrylates and of amphiphilic monomers comprising at least one fatty chain,
copolymers of hydrophilic methacrylates or acrylates and of hydrophobic monomers comprising at least one fatty chain, for instance the polyethylene glycol methacrylate/lauryl methacrylate copolymer,
associative polyurethanes.

Associative polyurethanes are nonionic block copolymers comprising in the chain both hydrophilic blocks usually of polyoxyethylene nature (polyurethanes may also be referred to as polyurethane polyethers), and hydrophobic blocks that may be aliphatic sequences alone and/or cycloaliphatic and/or aromatic sequences.

In particular, these polymers comprise at least two hydrocarbon-based lipophilic chains containing from 6 to 30 carbon atoms, separated by a hydrophilic block, the hydrocarbon-based chains possibly being pendent chains or chains at the end of the hydrophilic block. In particular, it is possible for one or more pendent chains to be envisaged. In addition, the polymer may comprise a hydrocarbon-based chain at one end or at both ends of a hydrophilic block.

Associative polyurethanes may be block polymers, in triblock or multiblock form. The hydrophobic blocks may thus be at each end of the chain (for example: triblock copolymer containing a hydrophilic central block) or distributed both at the ends and in the chain (for example: multiblock copolymer). These polymers may also be graft polymers or star polymers. Preferably, the associative polyurethanes are triblock copolymers in which the hydrophilic block is a polyoxyethylene chain comprising from 50 to 1000 oxyethylene groups. In general, associative polyurethanes comprise a urethane bond between the hydrophilic blocks, whence arises the name.

According to one preferred embodiment, a nonionic associative polymer of polyurethane type is used as gelling agent.

As examples of nonionic polyurethane polyethers that may not be used in the invention, mention may be made of the polymer $C_{16}$-$OE_{120}$-$C_{16}$ from the company Servo Delden (under the name SER AD FX1100, which is a molecule containing a urethane function and having a weight-average molecular weight of 1300), OE being an oxyethylene unit. Rheolate 205 bearing a urea function, sold by the company Rheox, or Rheolate 208 or 204, or alternatively Rheolate FX 1100 by Elementis, may also be used as associative polyurethane polymer. These associative polyurethanes are sold in pure form. The product DW 1206B from Rohm & Haas containing a $C_{20}$ alkyl chain and a urethane bond, sold at a solids content of 20% in water, may also be used.

It is also possible to use solutions or dispersions of these polymers, in particular in water or in aqueous-alcoholic medium. Examples of such polymers that may be mentioned include SER AD FX1010, SER AD FX1035 and SER AD 1070 from the company Servo Delden, and Rheolate 255, Rheolate 278 and Rheolate 244 sold by the company Rheox. It is also possible to use the products Aculyn 46, DW 1206F and DW 1206J, and also Acrysol RM 184 or Acrysol 44 from the company Rohm & Haas, or alternatively Borchigel LW 44 from the company Borchers, and mixtures thereof.

According to one preferred embodiment, the hydrophilic gelling agent is chosen from:
optionally modified hydroxypropyl guar, in particular hydroxypropyl guar modified with sodium methylcarboxylate groups (Jaguar XC97-1, Rhodia) or hydroxypropyltrimethylammonium guar chloride,
vinyl polymers, such as polyvinyl alcohol, anionic associative polymers derived from (meth)acrylic acid, such as the non-crosslinked copolymer obtained from methacrylic acid and steareth-20 methacrylate, sold under the name Aculyn 22 by Rohm & Haas, nonionic associative polymers of polyurethane polyether type, such as Steareth-100/PEG-136/HDI Copolymer sold under the name Rheolate FX 1100 by Elementis.

According to one preferred embodiment, the hydrophilic gelling agent is chosen from:

optionally modified hydroxypropyl guar, in particular hydroxypropyl guar modified with sodium methylcarboxylate groups (Jaguar XC97-1, Rhodia) or hydroxypropyltrimethylammonium guar chloride, anionic associative polymers derived from (meth)acrylic acid, such as the non-crosslinked copolymer obtained from methacrylic acid and steareth-20 methacrylate, sold under the name Aculyn 22 by Rohm & Haas, nonionic associative polymers of polyurethane polyether type, such as Steareth-100/PEG-136/HDI Copolymer sold under the name Rheolate FX 1100 by Elementis.

Amphoteric Associative Polymers

Among the associative amphoteric polymers of the invention, mention may be made of crosslinked or non-crosslinked, branched or unbranched amphoteric polymers, which may be obtained by copolymerization 1) of at least one monomer of formula (IVa) or (IVb):

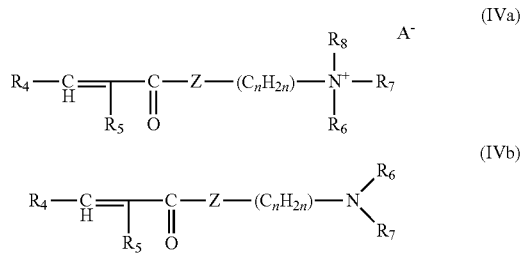

in which $R_4$ and $R_5$, which may be identical or different, represent a hydrogen atom or a methyl radical, $R_6$, $R_7$ and $R_8$, which may be identical or different, represent a linear or branched alkyl radical containing from 1 to 30 carbon atoms, Z represents a group NH or an oxygen atom, n is an integer from 2 to 5, $A^-$ denotes an anion derived from a mineral or organic acid, such as a methosulfate anion or a halide such as chloride or bromide.

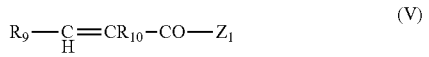

in which $R_9$ and $R_{10}$, which may be identical or different, represent a hydrogen atom or a methyl radical;

$Z_1$ represents a group OH or a group $NHC(CH_3)_2CH_2SO_3H$;

3) of at least one monomer of formula (VI):

in which $R_9$ and $R_{10}$, which may be identical or different, represent a hydrogen atom or a methyl radical, X denotes an oxygen or nitrogen atom and $R_{11}$ denotes a linear or branched alkyl radical containing from 1 to 30 carbon atoms;

4) optionally at least one crosslinking or branching agent;

at least one of the monomers of formula (IVa), (IVb) or (VI) comprising at least one fatty chain containing from 8 to 30 carbon atoms and the said compounds of the monomers of formulae (IVa), (IVb), (V) and (VI) possibly being quaternized, for example with a $C_1$-$C_4$ alkyl halide or a $C_1$-$C_4$ dialkyl sulfate.

The monomers of formulae (IVa) and (IVb) of the present invention are preferably chosen from the group formed by:

dimethylaminoethyl methacrylate, dimethylaminoethyl acrylate, diethylaminoethyl methacrylate, diethylaminoethyl acrylate, dimethylaminopropyl methacrylate, dimethylaminopropyl acrylate, dimethylaminopropylmethacrylamide or dimethylaminopropylacrylamide, optionally quaternized, for example with a $C_1$-$C_4$ alkyl halide or a $C_1$-$C_4$ dialkyl sulfate.

More particularly, the monomer of formula (IVa) is chosen from acrylamidopropyltrimethylammonium chloride and methacrylamidopropyltrimethylammonium chloride.

The compounds of formula (V) of the present invention are preferably chosen from the group formed by acrylic acid, methacrylic acid, crotonic acid, 2-methylcrotonic acid, 2-acrylamido-2-methylpropanesulfonic acid and 2-methacrylamido-2-methylpropanesulfonic acid. More particularly, the monomer of formula (V) is acrylic acid.

The monomers of formula (VI) of the present invention are preferably chosen from the group formed by $C_{12}$-$C_{22}$ and more particularly $C_{16}$-$C_{18}$ alkyl acrylates or methacrylates.

The crosslinking or branching agent is preferably chosen from N,N'-methylenebisacrylamide, triallylmethylammonium chloride, allyl methacrylate, n-methylolacrylamide, polyethylene glycol dimethacrylates, ethylene glycol dimethacrylate, diethylene glycol dimethacrylate, 1,6-hexanediol dimethacrylate and allyl sucrose.

The polymers according to the invention may also contain other monomers such as nonionic monomers and in particular $C_1$-$C_4$ alkyl acrylates or methacrylates.

The ratio of the number of cationic charges/anionic charges in these amphoteric polymers is preferably equal to about 1.

The weight-average molecular weights of the associative amphoteric polymers have a weight-average molecular mass of greater than 500, preferably between 10 000 and 10 000 000 and even more preferentially between 100 000 and 8 000 000.

Preferably, the associative amphoteric polymers of the invention contain from 1 mol % to 99 mol %, more preferentially from 20 mol % to 95 mol % and even more preferentially from 25 mol % to 75 mol % of compound(s) of formula (IVa) or (IVb). They also preferably contain from 1 mol % to 80 mol %, more preferentially from 5 mol % to 80 mol % and even more preferentially from 25 mol % to 75 mol % of compound(s) of formula (V). The content of compound(s) of formula (VI) is preferably between 0.1 mol % and 70 mol %, more preferentially between 1 mol % and 50 mol % and even more preferentially between 1 mol % and 10 mol %. The crosslinking or branching agent, when it is present, is preferably between 0.0001 mol % and 1 mol % and even more preferentially between 0.0001 mol % and 0.1 mol %.

Preferably, the mole ratio between the compound(s) of formula (IVa) or (IVb) and the compound(s) of formula (V) ranges from 20/80 to 95/5 and more preferentially from 25/75 to 75/25.

The associative amphoteric polymers according to the invention are described, for example, in patent application WO 98/44012.

The amphoteric polymers that are particularly preferred according to the invention are chosen from acrylic acid/acrylamidopropyltrimethylammonium chloride/stearyl methacrylate copolymers.

The hydrophilic gelling polymer(s), and in particular the associative polymers, may be present in the composition according to the invention in a total active material content ranging from 0.1% to 10% by weight and preferably from 0.5% to 5% by weight relative to the total weight of the composition.

It is understood that this amount is moreover liable to vary depending on whether the said polymer is or is not combined with an ionic and/or nonionic surfactant and/or a film-forming agent (other than alkylcellulose and in particular ethylcellulose), which are themselves also capable of acting on the consistency of the said composition.

Active Agents

The composition may also comprise at least one active agent chosen from moisturizers, cicatrizing agents and/or anti-ageing agents, for the skin and/or the lips, and in particular the lips.

According to this embodiment, the invention also relates to a process for caring for the skin and/or the lips, and in particular the lips, comprising the application of a composition according to the invention to the skin and/or the lips.

Moisturizers:

According to a first embodiment, the composition also comprises at least one moisturizer (also known as a humectant).

Moisturizers or humectants that may especially be mentioned include sorbitol, polyhydric alcohols, preferably of $C_2$-$C_8$ and more preferably $C_3$-$C_6$, preferably such as glycerol, propylene glycol, tripropylene glycol, 1,3-butylene glycol, dipropylene glycol and diglycerol, and mixtures thereof, glycerol and derivatives thereof, urea and derivatives thereof, especially Hydrovance® (2-hydroxyethylurea) sold by National Starch, lactic acids, hyaluronic acid, AHAs, BHAs, sodium pidolate, xylitol, serine, sodium lactate, ectoin and derivatives thereof, chitosan and derivatives thereof, collagen, plankton, an extract of Imperata cylindra sold under the name Moist 24® by the company Sederma, acrylic acid homopolymers, for instance Lipidure-HM® from NOF Corporation, β-glucan and in particular sodium carboxymethyl β-glucan from Mibelle-AG-Biochemistry; a mixture of passionflower oil, apricot oil, corn oil and rice bran oil sold by Nestle under the name NutraLipids®; a C-glycoside derivative such as those described in patent application WO 02/051 828 and in particular C-β-D-xylopyranoside-2-hydroxypropane in the form of a solution containing 30% by weight of active material in a water/propylene glycol mixture (60/40% by weight) such as the product manufactured by Chimex under the trade name Mexoryl SBB®; an oil of musk rose sold by Nestle; an extract of the microalga Prophyridium cruentum enriched with zinc, sold by Vincience under the name Algualane Zinc®; spheres of collagen and of chondroitin sulfate of marine origin (Ateocollagen) sold by the company Engelhard Lyon under the name Marine Filling Spheres; hyaluronic acid spheres such as those sold by the company Engelhard Lyon; and arginine.

Use will preferably be made of a moisturizer chosen from glycerol, urea and derivatives thereof, especially Hydrovance® sold by National Starch, hyaluronic acid, AHAs, BHAs, acrylic acid homopolymers, for instance Lipidure-HM® from NOF Corporation, β-glucan and in particular sodium carboxymethyl β-glucan from Mibelle-AG-Biochemistry; a mixture of passion flower oil, apricot oil, corn oil and rice bran oil sold by Nestle under the name NutraLipids®; a C-glycoside derivative such as those described in patent application WO 02/051 828 and in particular C-β-D-xylopyranoside-2-hydroxypropane in the form of a solution containing 30% by weight of active material in a water/propylene glycol mixture (60/40% by weight) such as the product sold by Chimex under the trade name Mexoryl SBB®; an oil of musk rose sold by Nestle; an extract of the microalga Prophyridium cruentum enriched with zinc, sold by Vincience under the name Algualane Zinc®; spheres of collagen and of chondroitin sulfate of marine origin (Ateocollagen) sold by the company Engelhard Lyon under the name Marine Filling Spheres; hyaluronic acid spheres such as those sold by the company Engelhard Lyon; and arginine.

Cicatrizing Agents

The active agent may also be chosen from cicatrizing agents.

Examples of cicatrizing agents that may especially be mentioned include: allantoin, urea, certain amino acids, for instance hydroxyproline, arginine, and serine, and also extracts of white lily (for instance Phytelene Lys 37EG 16295 from Indena), a yeast extract, for instance the cicatrizing agent LS LO/7225B from Laboratoires Serobiologiques) (Cognis), tamanu oil, extract of *Saccharomyces cerevisiae*, for instance Biodynes® TRF® from Arch Chemical, oat extracts, chitosan and derivatives, for instance chitosan glutamate, carrot extracts, artemia extract, for instance GP4G® from Vincience, sodium acexamate, lavandin extracts, propolis extracts, ximeninic acid and salts thereof, rose hip oil, marigold extracts, for instance Souci Ami® Liposoluble from Alban Muller, horsetail extracts, lemon peel extracts, for instance Herbasol® citron from Cosmetochem, helichrysum extracts, common yarrow extracts, folic acid, β-glucan derivatives, shea butter and purified fractions thereof, modified exopolysaccharides and alkylsulfone poly aminos accharides.

Anti-Ageing Agents

The active agent may also be chosen from anti-ageing agents, i.e. agents especially having a restructuring effect on the skin barrier, anti-glycation agents, active agents that stimulate the energy metabolism of cells, and mixtures thereof.

The agent with a restructuring effect on the skin barrier may be chosen from an extract of *Thermus thermophilus* such as Vénucéane® from Sederma, an extract of the rhizome of wild yam (*Dioscorea villosa*) such as Actigen Y® from Active Organics, plankton extracts, for instance Omega Plankton® from Secma, yeast extracts, for instance Relipidium® from Coletica, a chestnut extract such as Recoverine® from Silab, a cedar bud extract such as Gatuline Zen® from Gattefossé, sphingosines, for instance salicyloyl sphingosine sold under the name Phytosphingosine® SLC by the company Degussa, a mixture of xylitol, polyxylityl glycoside and xylitan, for instance Aquaxyl® from SEPPIC, extracts of Solanacea plants, for instance Lipidessence® from Coletica, and mixtures thereof.

Mention may also be made especially of ceramides, sphingoid-based compounds, glycosphingolipids, phospholipids, cholesterol and derivatives thereof, phytosterols, essential fatty acids, diacylglycerol, 4-chromanone and chromone derivatives, and mixtures thereof.

As preferred agents having a restructuring effect on the skin barrier function, mention will be made of an extract of *Thermus thermophilus*, an extract of the rhizome of wild yam (*Dioscorea villosa*), a yeast extract, a chestnut extract, a cedar bud extract, and mixtures thereof.

The term "anti-glycation agent" means a compound that prevents and/or reduces the glycation of skin proteins, in particular dermal proteins such as collagen.

Examples of anti-glycation agents include extracts of plants of the Ericacea family, such as an extract of blueberry (*Vaccinium angustifolium*), for example the product sold under the name Blueberry Herbasol Extract PG by the company Cosmetochem, ergothioneine and derivatives thereof, hydroxystilbenes and derivatives thereof, such as resveratrol and 3,3',5,5'-tetrahydroxystilbene (these anti-glycation agents are described in patent applications FR 2 802 425, FR 2 810 548, FR 2 796 278 and FR 2 802 420, respectively), dihydroxystilbenes and derivatives thereof, polypeptides of arginine and of lysine such as the product sold under the name Amadorine® by the company Solabia, carcinine hydrochloride (sold by Exsymol under the name Alistin®), an extract of *Helianthus annuus*, for instance Antiglyskin® from Silab, wine extracts such as the extract of powdered white wine on a maltodextrin support sold under the name Vin blanc déshydraté 2F by the company Givaudan, thioctic acid (or α-lipoic acid), a mixture of extract of bearberry and of marine glycogen, for instance Aglycal LS 8777® from Laboratoires Sérobiologiques, and an extract of black tea, for instance Kombuchka® from Sederma, and mixtures thereof.

The active agent for stimulating the energy metabolism of cells may be chosen, for example, from biotin, an extract of *Saccharomyces cerevisiae* such as Phosphovital® from Sederma, the mixture of sodium, manganese, zinc and magnesium salts of pyrrolidonecarboxylic acid, for instance Physiogenyl® from Solabia, a mixture of zinc, copper and magnesium gluconate, such as Sepitonic M3® from SEPPIC, and mixtures thereof.

The active agents used in the compositions according to the invention may be hydrophilic or lipophilic.

Preferably, the composition comprises at least one hydrophilic active agent, chosen from moisturizers, cicatrizing agents and anti-ageing agents.

Specifically, since the composition according to the invention comprises water, this water lends itself particularly to the introduction of hydrophilic active agents into the composition, in particular without any problem of stability of the composition and/or of the active agent. This is particularly interesting, in particular in the context of lipcare. Specifically, the standard lipstick compositions known in the prior art, whether they are solid or liquid, rarely comprise water, and, if they do contain any, they are generally unstable over time (i.e. they undergo phase separation or exudation).

Preferably, the active agent is chosen from: polyhydric alcohols, preferably of $C_2$-$C_8$ and more preferably of $C_3$-$C_6$, preferably such as glycerol, propylene glycol, 1,3-butylene glycol, dipropylene glycol, diglycerol, and a mixture thereof, hyaluronic acid, AHAs, BHAs, serine, collagen, a C-glycoside derivative and in particular C-β-D-xylopyranoside-2-hydroxypropane in the form of a solution containing 30% by weight of active material in a water/propylene glycol mixture (60/40 wt %); spheres of collagen and of chondroitin sulfate of marine origin (Ateocollagen), hyaluronic acid spheres; ceramides, preferably such as ceramide V.

Preferably, the active material content of the composition ranges from 0.001% to 30% by weight, preferably from 0.01% to 20% by weight, better still from 0.01% to 10% by weight, better still from 0.01% to 5% by weight and even better still from 0.05% to 1% by weight relative to the total weight of the composition.

A composition according to the invention may also comprise any additional component usually used in cosmetics, such as dyestuffs, fillers or cosmetic active agents.

Needless to say, a person skilled in the art will take care to select the optional additional compounds and/or the amount thereof such that the advantageous properties of the composition used according to the invention are not, or are not substantially, adversely affected by the envisaged addition.

Colorants

A composition in accordance with the present invention may comprise at least one dyestuff, which may be chosen from water-soluble or water-insoluble, liposoluble or non-liposoluble, organic or mineral dyestuffs, and materials with an optical effect, and mixtures thereof.

For the purposes of the present invention, the term "dyestuff" means a compound that is capable of producing a coloured optical effect when it is formulated in sufficient amount in a suitable cosmetic medium.

Preferably, the composition according to the invention comprises at least one dyestuff, chosen especially from pigments, nacres, and liposoluble and water-soluble dyes, and mixtures thereof.

According to one preferred embodiment, a composition according to the invention comprises at least one water-soluble dyestuff.

The water-soluble dyestuffs used according to the invention are more particularly water-soluble dyes.

For the purposes of the invention, the term "water-soluble dye" means any natural or synthetic, generally organic compound, which is soluble in an aqueous phase or water-miscible solvents and which is capable of colouring. In particular, the term "water-soluble" means the capacity of a compound to be dissolved in water, measured at 25° C., to a concentration at least equal to 0.1 g/l (production of a macroscopically isotropic, transparent, coloured or colourless solution). This solubility is in particular greater than or equal to 1 g/l.

As water-soluble dyes that are suitable for use in the invention, mention may be made especially of synthetic or natural water-soluble dyes, for instance FDC Red 4 (CI: 14700), DC Red 6 (Lithol Rubine Na; CI: 15850), DC Red 22 (CI: 45380), DC Red 28 (CI: 45410 Na salt), DC Red 30 (CI: 73360), DC Red 33 (CI: 17200), DC Orange 4 (CI: 15510), FDC Yellow 5 (CI: 19140), FDC Yellow 6 (CI: 15985), DC Yellow 8 (CI: 45350 Na salt), FDC Green 3 (CI: 42053), DC Green 5 (CI: 61570), FDC Blue 1 (CI: 42090).

As non-limiting illustrations of sources of water-soluble dyestuffs that may be used in the context of the present invention, mention may be made especially of those of natural origin, such as extracts of cochineal carmine, of beetroot, of grape, of carrot, of tomato, of annatto, of paprika, of henna, of caramel and of curcumin.

Thus, the water-soluble dyestuffs that are suitable for use in the invention are especially carminic acid, betanin, anthocyans, enocyanins, lycopene, β-carotene, bixin, norbixin, capxanthin, capsorubin, flavoxanthin, lutein, cryptoxanthin, rubixanthin, violaxanthin, riboflavin, rhodoxanthin, cantaxanthin and chlorophyll, and mixtures thereof.

They may also be copper sulfate, iron sulfate, water-soluble sulfopolyesters, rhodamine, methylene blue, the disodium salt of tartrazine and the disodium salt of fuchsin.

Some of these water-soluble dyestuffs are especially permitted for food use. Representatives of these dyes that may be mentioned more particularly include dyes of the carotenoid family, referenced under the food codes E120, E162, E163, E160a-g, E150a, E101, E100, E140 and E141.

According to one preferred variant, the water-soluble dyestuff(s) that are to be transferred onto the skin and/or the lips intended to be made up are formulated in a physiologically acceptable medium so as to be compatible with impregnation into the substrate.

The water-soluble dyestuff(s) may be present in a composition according to the invention in a content ranging from 0.01% to 8% by weight and preferably from 0.1% to 6% by weight relative to the total weight of the said composition.

According to a particularly preferred embodiment, the water-soluble dyestuff(s) are chosen from the disodium salt of brilliant yellow FCF sold by the company LCW under the name DC Yellow 6, the disodium salt of fuchsin acid D sold by the company LCW under the name DC Red 33, and the trisodium salt of Rouge Allura sold by the company LCW under the name FD & C Red 40.

According to one particular embodiment of the invention, the composition according to the invention comprises only water-soluble dyes as dyestuffs.

According to another embodiment, the composition according to the invention comprises at least one pigment and/or nacre as dyestuff.

According to another embodiment, a composition according to the invention may comprise, besides the water-soluble dyestuffs described previously, one or more additional dyestuffs, especially such as pigments or nacres, conventionally used in cosmetic compositions.

The term "pigments" should be understood as meaning white or coloured, inorganic (mineral) or organic particles, which are insoluble in the liquid organic phase, and which are intended to colour and/or opacify the composition and/or the deposit produced with the composition.

The pigments may be chosen from mineral pigments, organic pigments and composite pigments (i.e. pigments based on mineral and/or organic materials).

The pigments may be chosen from monochromatic pigments, lakes, nacres, and pigments with an optical effect, for instance reflective pigments and goniochromatic pigments.

The mineral pigments may be chosen from metal oxide pigments, chromium oxides, iron oxides, titanium dioxide, zinc oxides, cerium oxides, zirconium oxides, manganese violet, Prussian blue, ultramarine blue and ferric blue, and mixtures thereof.

The organic pigments may be, for example:
cochineal carmine,
organic pigments of azo dyes, anthraquinone dyes, indigoid dyes, xanthene dyes, pyrene dyes, quinoline dyes, triphenylmethane dyes and fluorane dyes;
organic lakes or insoluble sodium, potassium, calcium, barium, aluminium, zirconium, strontium or titanium salts of acidic dyes such as azo, anthraquinone, indigoid, xanthene, pyrene, quinoline, triphenylmethane or fluorane dyes. These dyes generally comprise at least one carboxylic or sulfonic acid group;
melanin-based pigments.

Among the organic pigments, mention may be made of D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5 and FD&C Yellow No. 6.

The hydrophobic treatment agent may be chosen from silicones such as methicones, dimethicones and perfluoroalkylsilanes; fatty acids such as stearic acid; metal soaps such as aluminium dimyristate, the aluminium salt of hydrogenated tallow glutamate, perfluoroalkyl phosphates, perfluoroalkylsilanes, perfluoroalkylsilazanes, polyhexafluoropropylene oxides, polyorganosiloxanes comprising perfluoroalkyl perfluoropolyether groups, amino acids, N-acylamino acids or salts thereof; lecithin, isopropyl triisostearyl titanate, and mixtures thereof.

The N-acylamino acids may comprise an acyl group containing from 8 to 22 carbon atoms, for instance a 2-ethylhexanoyl, caproyl, lauroyl, myristoyl, palmitoyl, stearoyl or cocoyl group. The salts of these compounds may be aluminium, magnesium, calcium, zirconium, zinc, sodium or potassium salts. The amino acid may be, for example, lysine, glutamic acid or alanine.

The term "alkyl" mentioned in the compounds cited above especially denotes an alkyl group containing from 1 to 30 carbon atoms and preferably containing from 5 to 16 carbon atoms.

Hydrophobic-treated pigments are described especially in patent application EP-A-1 086 683.

For the purposes of the present patent application, the term "nacre" should be understood as meaning coloured particles of any form, which may or may not be iridescent, especially produced by certain molluscs in their shell, or alternatively synthesized, and which have a colour effect via optical interference.

Examples of nacres that may be mentioned include nacreous pigments such as titanium mica coated with an iron oxide, mica coated with bismuth oxychloride, titanium mica coated with chromium oxide, titanium mica coated with an organic dye especially of the abovementioned type, and also nacreous pigments based on bismuth oxychloride. They may also be mica particles at the surface of which are superimposed at least two successive layers of metal oxides and/or of organic colourants.

The nacres may more particularly have a yellow, pink, red, bronze, orange, brown, gold and/or coppery colour or glint.

As illustrations of nacres that may be introduced as interference pigments into the first composition, mention may be made especially of the gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the pink nacres sold especially by the company Engelhard under the name Tan opale G005 (Gemtone); the black nacres with a gold tint sold especially by the company Engelhard under the name Nu antique bronze 240 AB (Timica), the blue nacres sold especially by the company Merck under the name Matte blue (17433) (Microna), the white nacres with a silvery tint sold especially by the company Merck under the name Xirona Silver, and the golden-green pink-orange nacres sold especially by the company Merck under the name Indian summer (Xirona), and mixtures thereof.

The composition according to the invention may also be free of dyestuff. According to this embodiment, the composition may be a care composition, preferably for the skin or the lips.

According to this embodiment, the composition according to the invention may advantageously be a lip balm.

Fillers

A cosmetic composition used according to the invention may also comprise at least one filler, of organic or mineral nature.

The term "filler" should be understood to mean colourless or white solid particles of any shape which are in a form that is insoluble and dispersed in the medium of the composition. These particles, of mineral or organic nature, can give body or rigidity to the composition and/or softness and uniformity to the makeup. They are different from dyestuffs.

Among the fillers that may be used in the compositions according to the invention, mention may be made of silica, kaolin, bentone, starch, lauroyllysine, and fumed silica particles, optionally hydrophilic- or hydrophobic-treated, and mixtures thereof.

A composition used according to the invention may comprise one or more fillers in a content ranging from 0.1% to 15% by weight relative to the total weight of the composition and in particular from 1% to 10% by weight relative to the total weight of the composition.

Preferably, a composition according to the invention comprises at least one compound chosen from fillers, waxes, pasty fatty substances, semi-crystalline polymers and/or lipophilic gelling agents, and mixtures thereof.

Usual Additional Cosmetic Ingredients

A composition used according to the invention may also comprise any usual cosmetic ingredient, which may be chosen especially from antioxidants, additional film-forming polymers (lipophilic or hydrophilic) other than alkylcellulose and in particular ethylcellulose, fragrances, preserving agents, neutralizers, sunscreens, sweeteners, vitamins, free-radical scavengers and sequestrants, and mixtures thereof.

Needless to say, a person skilled in the art will take care to select the optional additional ingredients and/or the amount thereof such that the advantageous properties of the composition according to the invention are not, or are not substantially, adversely affected by the envisaged addition.

A composition according to the invention may more particularly be a composition for making up and/or caring for the skin and/or the lips, in particular the lips.

A composition according to the invention may constitute a liquid lipstick for the lips, a body makeup product, a facial or body care product or an antisun product.

According to a preferred embodiment, a composition of the invention is in liquid form. As illustrations of liquid formulations, mention may be made especially of lip glosses. In particular, the composition according to the invention may be a lip stain.

The composition according to the invention may preferably be applied using an applicator, for example a brush.

According to one particularly preferred embodiment, the composition according to the invention is an oil-in-water emulsion.

The composition according to the invention may be manufactured via the known processes generally used in cosmetics or dermatology.

As stated previously, the composition according to the invention is homogeneous and gives access to a deposit that has good cosmetic properties, in particular in terms of gloss, comfort, no sensation of pulling and fresh, fine and light deposit.

The present invention will be understood more clearly by means of the examples that follow.

These examples are given as illustrations of the invention and cannot be interpreted as limiting its scope.

EXAMPLE 1: LIPSTICKS IN THE FORM OF LIP STAIN

The following liquid lipstick composition was prepared. Composition 1 according to the invention comprises water, ethylcellulose, a first non-volatile hydrocarbon-based oil (octyldodecanol), a second non-volatile silicone oil (Belsil 1000), a third hydrocarbon-based oil and a surfactant.

| Compounds (Chemical Name/Commercial Reference) | Example 1 according to the invention (weight %) |
| --- | --- |
| Ethylcellulose at 26.2% in water; sodium lauryl sulfate (1.3%) and cetyl alcohol (2.5%) Aquacoat ECD 30 from FMC Biopolymer | 9.6 |
| Octyldodecanol | 7.1 |
| Trimethylsiloxyphenyl Dimethicone (Belsil PDM 1000 from Wacker) | 15 |
| Hydrogenated polyisobutene (Parleam from NOF Corporation) | 6.8 |
| Water | qs 100 |
| Ethanol | 3 |
| Mixture of sorbitan stearate and sucrose cocoate (Arlacel 2121U-FL from Croda) | 4 |
| Hydroxypropyl guar (Jaguar HP 105 from Rhodia) | 0.5 |
| Phenoxyethanol | 0.5 |
| Red 7 | 1 |
| Total: | 100 |

Preparation Protocol:
1) The fatty phase composed of the phenyl silicone oil, the Parleam oil and pigments previously ground in 3/7 of octyldodecanol was heated to 55° C. in a heating pan.
2) The surfactant was added and the mixture was stirred at 55° C. until homogeneous.
3) The ethylcellulose and the octyldodecanol were poured into a beaker. The mixture was then stirred using a Rayneri-type deflocculator for 1 hour at 55° C., followed by addition of the water, the gelling agent and the preserving agent, and the mixture was stirred with the Rayneri deflocculator at 55° C. until a homogeneous mixture was obtained.

4) In a second heating pan, this mixture was then poured into the fatty phase and stirred (Rayneri deflocculator) until the mixture reached room temperature. The ethanol was then added and the mixture was stirred for 5 minutes.

5) The product was finally packaged in lip gloss pots.

After 24 hours at room temperature, the compositions obtained were evaluated and their viscosity was measured according to the protocol described previously.

The stability of the compositions was evaluated by placing the compositions obtained for 72 hours at 24° C. and for 72 hours at 45° C. The compositions were especially checked to see if phase separation, the formation of grains or a variation in viscosity was observed.

| Evaluation of the Compositions | Example 1 According to the invention |
|---|---|
| Appearance of the composition | The composition is uniform and stable at 24° C. and at 45° C. |
| Form and viscosity of the composition (Pa · s) Spindle 2 | Liquid of viscosity 0.3 Pa · s |

Compositions 1 and 2 according to the invention produced a lipstick in liquid form for the lips. The composition obtained is homogeneous.

Each of the compositions was applied to the lips with a lip gloss applicator so as to form a deposit of uniform thickness; the ease of application and the appearance of the deposit were evaluated. Furthermore, the tacky nature of the deposit was evaluated during drying of the formulation after 2 minutes at room temperature. To do this, a finger was applied, after the specified drying time, onto the applied formula and the tack was assessed by the person on removal of his finger from the applied formulation.

For composition 1 according to the invention, the application to the lips is easy (glidant on application and easy application). The deposits obtained are homogeneous, light, fine and fresh. Furthermore, the deposits obtained are sparingly tacky, do not migrate and are satisfactorily glossy.

The invention claimed is:

1. A liquid cosmetic composition for making up and/or caring for the lips comprising, in a physiologically acceptable medium for lips:
   an aqueous phase comprising at least 20% of water;
   1% to 60% by weight, relative to the total weight of the composition, of ethylcellulose;
   5% to 40% by weight, relative to the total weight of the composition, of at least one first hydrocarbon-based non-volatile oil that is octyldodecanol;
   15% to 30% by weight, relative to the total weight of the composition, of at least one second non-volatile oil liquid at a temperature of 25° C. and an atmospheric pressure of 760 mmHg, chosen from phenyl silicone oils;
   2% to 20% by weight relative to the total weight of the composition of at least one third non-volatile oil liquid at a temperature of 25° C. and an atmospheric pressure of 760 mmHg, the said third oil being chosen from liquid paraffin, liquid petroleum jelly, polybutylenes, hydrogenated polyisobutylenes, decene/butene copolymers, polybutene/polyisobutene copolymers, polydecenes and hydrogenated polydecenes, and mixtures thereof;
   at least one dyestuff; and
   at least one nonionic surfactant,
   wherein said composition is free of silicone surfactant and wherein the at least one dyestuff is present in an amount sufficient to produce a colored optical effect upon application to the lips sufficient to make up the lips wherein the composition is not a sunscreen.

2. The composition as claimed in claim 1, said composition being in the form of an oil-in-water emulsion.

3. The composition as claimed in claim 1, said composition having a viscosity at 20° C. of from 0.05 to 1.5 Pa·s.

4. The composition as claimed in claim 1, comprising from 2% to 30% by weight, relative to the total weight of the composition, of ethylcellulose.

5. The composition as claimed in claim 1, wherein the first non-volatile hydrocarbon-based first oil and the ethylcellulose are present in a first non-volatile hydrocarbon-based oil(s)/ethylcellulose weight ratio of from 0.5 to 20.

6. The composition as claimed in claim 1, wherein the third oil is selected from the group consisting of polydecene, hydrogenated polydecene, and mixtures thereof.

7. The composition as claimed in claim 1, comprising from 20% to 95% by weight of water, relative to the total weight of the composition.

8. The composition as claimed in claim 1, comprising:
   from 2% to 30% by weight of ethylcellulose, and
   from 30% to 85% by weight of water,
   all weights being relative to the total weight of the composition.

9. The composition as claimed in claim 1, wherein the total content of surfactant(s) is from 0.1% to 20% by weight, relative to the total weight of the composition.

10. The composition as claimed in claim 1, wherein the weight ratio of non-volatile oils to surfactant(s) is from 1 to 40.

11. The composition as claimed in claim 1, wherein the weight ratio of non-volatile oils to surfactant(s) is from 3 to 35.

12. The composition as claimed in claim 1, wherein the weight ratio of non-volatile oils to surfactant(s) is from 4 to 25.

13. The composition as claimed in claim 1, comprising at least one compound chosen from fillers, waxes, hydrophilic gelling agents, pasty fatty substances, semi-crystalline polymers and/or lipophilic gelling agents, and mixtures thereof.

14. The composition as claimed in claim 1, further comprising ethanol.

15. The composition as claimed in claim 1, the said composition being a lip gloss or a lip stain.

16. Cosmetic process for making up and/or caring for the lips, comprising at least one step that consists in applying to the lips at least one composition as defined in claim 1.

* * * * *